United States Patent
Kim et al.

(10) Patent No.: US 11,557,728 B2
(45) Date of Patent: Jan. 17, 2023

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Chi-Sik Kim, Gyeonggi-do (KR); Young-Gil Kim, Gyeonggi-do (KR); Hong-Se Oh, Gyeonggi-do (KR); Dong-Hyung Lee, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 0 days.

(21) Appl. No.: 16/908,922

(22) Filed: Jun. 23, 2020

(65) Prior Publication Data
US 2021/0013418 A1    Jan. 14, 2021

(30) Foreign Application Priority Data

Jul. 9, 2019 (KR) .................. 10-2019-0082765

(51) Int. Cl.
| | | |
|---|---|---|
| H01L 51/00 | (2006.01) |
| C07C 13/62 | (2006.01) |
| C09K 11/06 | (2006.01) |
| C07D 307/91 | (2006.01) |
| H01L 51/50 | (2006.01) |

(52) U.S. Cl.
CPC .......... *H01L 51/0058* (2013.01); *C07C 13/62* (2013.01); *C07D 307/91* (2013.01); *C09K 11/06* (2013.01); *H01L 51/0055* (2013.01); *H01L 51/0073* (2013.01); *C07C 2603/24* (2017.05); *C07C 2603/52* (2017.05); *C09K 2211/1007* (2013.01); *C09K 2211/1011* (2013.01); *C09K 2211/1018* (2013.01); *H01L 51/5012* (2013.01); *H01L 51/5016* (2013.01)

(58) Field of Classification Search
CPC ..................................................... C07C 13/62
See application file for complete search history.

(56) References Cited

U.S. PATENT DOCUMENTS

2021/0269405 A1*  9/2021  Lee .................... H01L 51/0067

FOREIGN PATENT DOCUMENTS

KR            101423070 B1      7/2014

* cited by examiner

*Primary Examiner* — Zinna Northington Davis
(74) *Attorney, Agent, or Firm* — G. Creston Campbell

(57) ABSTRACT

The present disclosure relates to an organic electroluminescent compound and an organic electroluminescent device comprising the same. The organic electroluminescent device having improved driving voltage and/or current efficiency characteristics can be provided by comprising the organic electroluminescent compound according to the present disclosure.

6 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent (EL) device is a self-light-emitting device which has advantages in that it provides a wider viewing angle, a greater contrast ratio, and a faster response time. An organic EL device was first developed by Eastman Kodak in 1987, by using small aromatic diamine molecules and aluminum complexes as materials for forming a light-emitting layer [Appl. Phys. Lett. 51, 913, 1987].

An organic electroluminescent device (OLED) changes electric energy into light by applying electricity to an organic light-emitting material, and commonly comprises an anode, a cathode, and an organic layer formed between the two electrodes. The organic layer of the OLED may comprise a hole injection layer, a hole transport layer, a hole auxiliary layer, a light-emitting auxiliary layer, an electron blocking layer, a light-emitting layer (containing host and dopant materials), an electron buffer layer, a hole blocking layer, an electron transport layer, an electron injection layer, etc. The materials used in the organic layer can be classified into a hole injection material, a hole transport material, a hole auxiliary material, a light-emitting auxiliary material, an electron blocking material, a light-emitting material, an electron buffer material, a hole blocking material, an electron transport material, an electron injection material, etc., depending on functions. In the OLED, due to an application of a voltage, holes are injected from the anode to the light-emitting layer, electrons are injected from the cathode to the light-emitting layer, and excitons of high energies are formed by a recombination of the holes and the electrons. From this energy, organic luminescent compounds reach an excited state, and light emission occurs by emitting light from energy as the excited state of the organic luminescent compounds returns to a ground state.

Recently, according to larger area of displays, light-emitting materials which can exhibit more delicate and vivid colors are required. Specifically, in the case of blue light-emitting materials, materials such as ADN and DPVBi are used as a host material, and materials such as aromatic amine-based compounds, copper phthalocyanine compounds, carbazole-based derivatives, perylene-based derivatives, coumarin-based derivatives, and pyrene-based derivatives are used as a dopant material. However, these materials are difficult to obtain a deep blue color with high color purity, and are problematic due to having poorer current efficiency as the wavelength gets shorter.

Accordingly, in realizing a full color display, developments of light-emitting materials of deep blue having excellent current efficiency and other organic materials having a suitable energy level with the blue light-emitting material are required.

KR Patent No. 1423070 discloses an organic electroluminescent compound comprising an anthracene moiety. However, this reference does not specifically disclose an organic electroluminescent compound of the present disclosure comprising an aromatic moiety in which biphenyl and naphthalene are fused.

DISCLOSURE OF INVENTION

Technical Problems

The objective of the present disclosure is firstly to provide an organic electroluminescent compound effective for producing an organic electroluminescent device having low driving voltage and/or high current efficiency characteristics. Second is to provide an organic electroluminescent device comprising the organic electroluminescent compound.

Solution to Problem

Blue light-emitting organic electroluminescent devices that have been generally used so far have lower current efficiency than green and red light-emitting organic electroluminescent devices. This is because the blue light-emitting organic electroluminescent device uses a fluorescent dopant. The energy transfer mechanism in fluorescent materials follows Förster energy transfer. In Förster energy transfer, light emission of a host is important in exciting a dopant. That is, as the light emission of the host increases, the current efficiency of the organic electroluminescent device increases. In order to increase the light emission of the host, it is generally necessary to reduce a quenching of the host light emission, and it is considered that the quenching of the host light emission is due to the stacking of the host. The present inventors have introduced a bulky aromatic moiety in which biphenyl and naphthalene are fused as a substituent after studying in order to interrupt the stacking of the host. As a result, it was confirmed that the current efficiency of the blue organic electroluminescent device was improved. In addition, it is believed that since the aromatic moiety of the present disclosure in which biphenyl and naphthalene are fused comprises a naphthalene structure which is excellent in light emission, it is possible to more effectively increase the current efficiency of the blue light-emitting organic electroluminescent device. Specifically, the present inventors have completed the present invention by finding that the organic electroluminescent compound represented by the following formula 1 achieves the aforementioned objective.

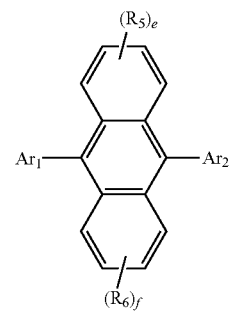

(1)

wherein $Ar_1$ represents a substituted or unsubstituted (C6-C30) aryl, or a substituted or unsubstituted (5- to 30-membered) heteroaryl;

R$_5$ and R$_6$ each independently represent hydrogen, deuterium, a halogen, a cyano, a substituted or unsubstituted (C1-C30)alkyl, a substituted or unsubstituted (C6-C30)aryl, or a substituted or unsubstituted (5- to 30-membered)heteroaryl;

Ar$_2$ represents

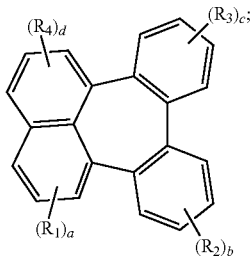

wherein Ar$_2$ is linked to

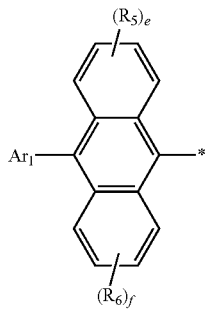

at one of the positions R$_1$ to R$_4$ (* represents the position linked to Ar$_2$), and R$_1$ to R$_4$ not linked to

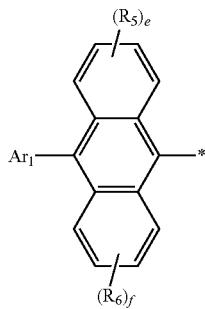

each independently represent hydrogen, deuterium, a halogen, a cyano, a substituted or unsubstituted (C1-C30)alkyl, a substituted or unsubstituted (C6-C30)aryl, or a substituted or unsubstituted (5-30 membered) heteroaryl;

a and d each independently represent an integer of 1 to 3, and b, c, e and f each independently represent an integer of 1 to 4;

wherein if a to f are integers of 2 or more, each R$_1$ to each R$_6$ may be the same or different from each other.

Advantageous Effects of Invention

By using the organic electroluminescent compound according to the present disclosure, it is possible to produce an organic electroluminescent device having improved driving voltage and/or current efficiency characteristics.

MODE FOR THE INVENTION

Hereinafter, the present disclosure will be described in detail. However, the following description is intended to explain the invention, and is not meant in any way to restrict the scope of the invention.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, an electron injection material, etc.

The organic electroluminescent material of the present disclosure may comprise at least one compound represented by formula 1. The compound represented by formula 1 may be comprised in a light-emitting layer, but is not limited thereto. When comprised in a light-emitting layer, the compound represented by formula 1 may be comprised as a host such as a host for blue light-emission. According to one embodiment of the present disclosure, the compound of formula 1 may be a fluorescent host, for example, a fluorescent host for blue light-emission.

Hereinafter, the compound represented by formula 1 will be described in more detail.

Herein, the term "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, iso-propyl, n-butyl, iso-butyl, tert-butyl, etc. The term "(C2-C30)alkenyl" is meant to be a linear or branched alkenyl having 2 to 30 carbon atoms constituting the chain, in which the number of carbon atoms is preferably 2 to 20, and more preferably 2 to 10. The above alkenyl may include vinyl, 1-propenyl, 2-propenyl, 1-butenyl, 2-butenyl, 3-butenyl, 2-methylbut-2-enyl, etc. The term "(C2-C30)alkynyl" is meant to be a linear or branched alkynyl having 2 to 30 carbon atoms constituting the chain, in which the number of carbon atoms is preferably 2 to 20, and more preferably 2 to 10. The above alkynyl may include ethynyl, 1-propynyl, 2-propynyl, 1-butynyl, 2-butynyl, 3-butynyl, 1-methylpent-2-ynyl, etc. The term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. The term "(3- to 7-membered)heterocycloalkyl" is meant to be a cycloalkyl having 3 to 7, preferably 5 to 7, ring backbone atoms, and including at least one heteroatom selected from the group consisting of B, N, O, S, Si, and P, preferably the group consisting of O, S, and N. The above heterocycloalkyl may include tetrahydrofuran, pyrrolidine, thiolan, tetrahydropyran, etc. The term "(C6-C30)aryl" is meant to be a monocyclic or fused ring radical derived from an aromatic hydrocarbon having 6 to 30 ring backbone carbon atoms, in which the number of the ring backbone carbon atoms is preferably 6 to 25, more preferably 6 to 18. The above aryl may be partially saturated, and may comprise a spiro structure. The above aryl may include phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, azulenyl, etc. More specifically, the aryl may include phenyl, 1-naphthyl, 2-naphthyl, 1-anthryl, 2-anthryl, 9-anthryl, benzanthryl, 1-phenanthryl, 2-phenanthryl, 3-phenanthryl, 4-phenanthryl, 9-phenanthryl, naphthacenyl, pyrenyl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 1-fluorenyl, 2-fluorenyl, 3-fluorenyl, 4-fluorenyl, 9-fluorenyl, benzofluorenyl, dibenzofluorenyl, 2-biphenylyl, 3-biphenylyl, 4-biphenylyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 3-fluoranthenyl, 4-fluoranthenyl, 8-fluoranthenyl, 9-fluoranthenyl, benzofluoranthenyl, o-tolyl, m-tolyl, p-tolyl, 2,3-xylyl, 3,4-xylyl, 2,5-xylyl, mesityl, o-cumenyl, m-cumenyl, p-cumenyl, p-t-butylphenyl, p-(2-phenylpropyl)phenyl, 4'-methylbiphenylyl, 4"-t-butyl-p-terphenyl-4-yl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, etc.

Herein, the term "(3- to 30-membered)heteroaryl" is an aryl group having 3 to 30 ring backbone atoms, and including at least one, preferably 1 to 4 heteroatoms selected from the group consisting of B, N, O, S, Si, and P. The above heteroaryl may be a monocyclic ring, or a fused ring condensed with at least one benzene ring; may be partially saturated; may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl such as benzofuranyl, benzothiophenyl, isobenzofuranyl, dibenzofuranyl, dibenzothiophenyl, benzonaphthofuranyl, benzonaphthothiophenyl, benzimidazolyl, benzothiazolyl, naphthothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, dihydroacridinyl, etc. More specifically, the heteroaryl may include 1-pyrrolyl, 2-pyrrolyl, 3-pyrrolyl, pyrazinyl, 2-pyridinyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolidinyl, 2-indolidinyl, 3-indolidinyl, 5-indolidinyl, 6-indolidinyl, 7-indolidinyl, 8-indolidinyl, 2-imidazopyridinyl, 3-imidazopyridinyl, 5-imidazopyridinyl, 6-imidazopyridinyl, 7-imidazopyridinyl, 8-imidazopyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazolyl-1-yl, azacarbazolyl-2-yl, azacarbazolyl-3-yl, azacarbazolyl-4-yl, azacarbazolyl-5-yl, azacarbazolyl-6-yl, azacarbazolyl-7-yl, azacarbazolyl-8-yl, azacarbazolyl-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, a 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, etc. "Halogen" includes F, Cl, Br, and I.

In addition, "ortho (o-)," "meta (m-)," and "para (p-)" are prefixes, which represent the relative positions of substituents, respectively. Ortho indicates that two substituents are adjacent to each other, and for example, when two substituents in a benzene derivative occupy positions 1 and 2, it is called an ortho position. Meta indicates that two substituents are at positions 1 and 3, and for example, when two substituents in a benzene derivative occupy positions 1 and 3, it is called a meta position. Para indicates that two substituents are at positions 1 and 4, and for example, when two substituents in a benzene derivative occupy positions 1 and 4, it is called a para position.

Herein, "substituted" in the expression "substituted or unsubstituted" means that a hydrogen atom in a certain functional group is replaced with another atom or another functional group, i.e., a substituent. The substituents of the substituted alkyl, the substituted aryl, and the substituted heteroaryl in $R_1$ to $R_6$, and $Ar_1$ each independently are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with a (C6-C30)aryl(s); a (C6-C30)aryl unsubstituted or substituted with at least one of deuterium, a (C1-C30)alkyl(s) and a (3- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl (C6-C30)aryl. According to one embodiment of the present disclosure, the substituents each independently are at least one selected from the group consisting of deuterium, a (C1-C6)alkyl, a (C6-C12)aryl unsubstituted or substituted with one or more deuterium, and a (5- to 15-membered) heteroaryl. Specifically, the substituents each independently may be at least one selected from the group consisting of deuterium, a methyl, a tert-butyl, a phenyl, a naphthyl, a phenyl substituted with one or more deuterium, and a carbazolyl.

The compound represented by formula 1 may be represented by the following formula 1-1 or 1-2:

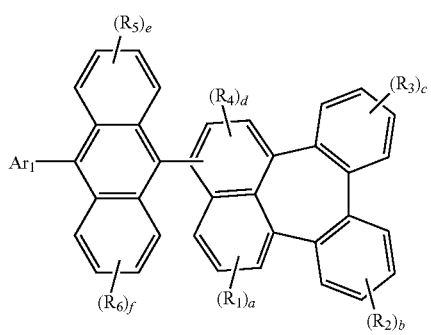

(1-1)

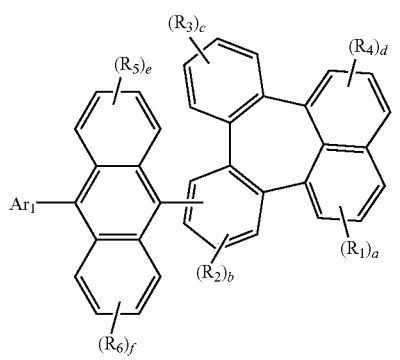

(1-2)

wherein
$R_1$ to $R_6$, $Ar_1$, and a to f are as defined in formula 1, with a proviso that d is 1 or 2 in formula 1-1 and b is 1, 2, or 3 in formula 1-2.

In formula 1, $Ar_1$ represents a substituted or unsubstituted (C6-C30)aryl, or a substituted or unsubstituted (5- to 30-membered)heteroaryl. According to one embodiment of the present disclosure, $Ar_1$ is a substituted or unsubstituted (C6-C24)aryl or a substituted or unsubstituted (5- to 20-membered)heteroaryl. According to another embodiment of the present disclosure, $Ar_1$ is a (C6-C24)aryl unsubstituted or substituted with one or more selected from deuterium, a (C1-C6)alkyl(s), a (C6-C12)aryl(s), a (C6-C12) aryl(s) substituted with deuterium, and a (5- to 15-membered)heteroaryl(s); or a (5- to 20-membered)heteroaryl unsubstituted or substituted with one or more selected from deuterium, a (C6-C12)aryl(s), and a (C6-C12)aryl(s) substituted with deuterium. For example, $Ar_1$ may be phenyl, naphthyl, biphenyl, phenanthrenyl, terphenyl, triphenylenyl, naphthylphenyl, phenylnaphthyl, phenylphenanthrenyl, diphenylfluorenyl, diphenylbenzofluorenyl, phenyl substituted with one or more deuterium, biphenyl substituted with one or more deuterium, naphthyl substituted with one or more deuterium, phenylnaphthyl substituted with one or more deuterium, phenyl substituted with tert-butyl, dimethylfluorenyl, dimethylbenzofluorenyl, phenyl substituted with carbazolyl, dibenzofuranyl, dibenzothiophenyl, benzonaphthofuranyl, benzonaphthothiophenyl, dibenzofuranyl substituted with one or more deuterium, benzofuranyl substituted with phenyl, benzothiophenyl substituted with phenyl, benzoxazolyl substituted with phenyl, carbazolyl substituted with phenyl, naphthoxazolyl substituted with phenyl, phenylnaphthoxazolyl substituted with one or more deuterium, etc.

In formula 1, $Ar_2$ represents

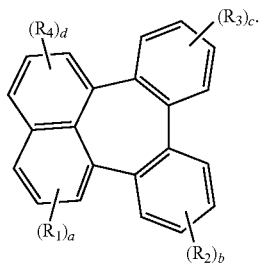

In formula 1, $Ar_2$ is linked to

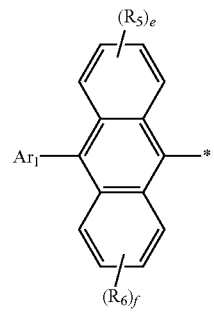

at one of the positions $R_1$ to $R_4$ (* represents the position linked to $Ar_2$). $R_1$ to $R_4$ not linked to

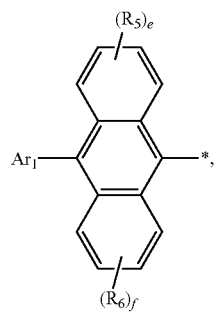

and $R_5$ and $R_6$ each independently represent hydrogen, deuterium, a halogen, a cyano, a substituted or unsubstituted (C1-C30)alkyl, a substituted or unsubstituted (C6-C30)aryl, or a substituted or unsubstituted (5- to 30-membered)heteroaryl. According to one embodiment of the present disclosure, $R_1$ to $R_4$ not linked to

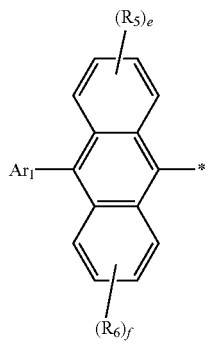

each independently are hydrogen, deuterium, or a substituted or unsubstituted (C6-C12)aryl, and $R_5$ and $R_6$ each independently are hydrogen or deuterium. According to another embodiment of the present disclosure, $R_1$ to $R_4$ not linked to

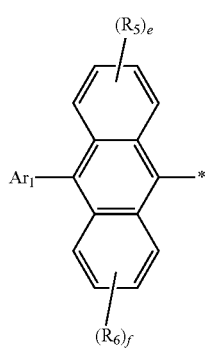

each independently are hydrogen, deuterium, or an unsubstituted (C6-C12)aryl, and $R_5$ and $R_6$ each independently are hydrogen or deuterium. For example, $R_1$ to $R_4$ not linked to

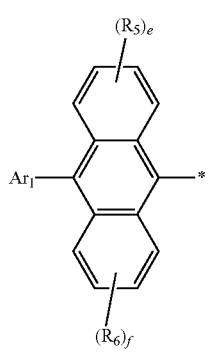

may be each independently hydrogen, deuterium, phenyl, etc.

According to one embodiment of the present disclosure, in formula 1, $Ar_1$ is a substituted or unsubstituted (C6-C24) aryl, or a substituted or unsubstituted (5- to 20-membered) heteroaryl; $R_1$ to $R_4$ not linked to

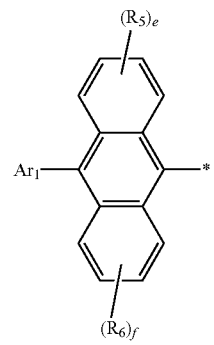

each independently are hydrogen, deuterium, or a substituted or unsubstituted (C6-C12)aryl; and $R_5$ and $R_6$ each independently are hydrogen or deuterium.

According to another embodiment of the present disclosure, in formula 1, $Ar_1$ is a (C6-C24)aryl unsubstituted or substituted with one or more selected from deuterium, a (C1-C6)alkyl(s), a (C6-C12)aryl(s), a (C6-C12)aryl(s) substituted with deuterium, and a (5- to 15-membered)heteroaryl(s); or a (5- to 20-membered)heteroaryl unsubstituted or substituted with one or more selected from deuterium, a (C6-C12)aryl(s), and a (C6-C12)aryl(s) substituted with deuterium; $R_1$ to $R_4$ not linked to

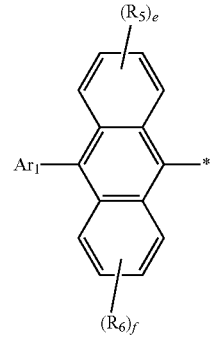

each independently are hydrogen, deuterium, or an unsubstituted (C6-C12)aryl; and $R_5$ and $R_6$ each independently are hydrogen or deuterium.

In the formulas of the present disclosure, if adjacent substituents are linked to each other to form a ring, the ring may be a substituted or unsubstituted mono- or polycyclic (3- to 30-membered) alicyclic or aromatic ring, or the combination thereof, in which the formed ring may contain at least one heteroatom selected from B, N, O, S, Si, and P, preferably N, O, and S. According to one embodiment of the present disclosure, the number of the ring backbone atoms may be 5 to 20. According to another embodiment of the present disclosure, the number of the ring backbone atoms may be 5 to 15. For example, the fused ring may be a substituted or unsubstituted dibenzothiophene ring, a substituted or unsubstituted dibenzofuran ring, a substituted or unsubstituted naphthalene ring, a substituted or unsubstituted phenanthrene ring, a substituted or unsubstituted fluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, or a substituted or unsubstituted carbazole ring.

In the formulas of the present disclosure, the heteroaryl (ene), each independently, may contain at least one heteroatom selected from B, N, O, S, Si, and P. In addition, the heteroatom may be bonded to at least one substituent(s) selected from the group consisting of hydrogen, deuterium, a halogen, a cyano, a substituted or unsubstituted (C1-C30) alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

The compound represented by formula 1 includes the following compounds, but is not limited thereto.

C-1
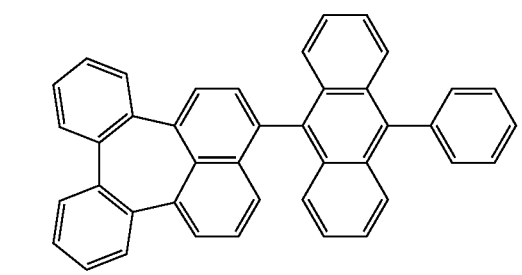

C-2
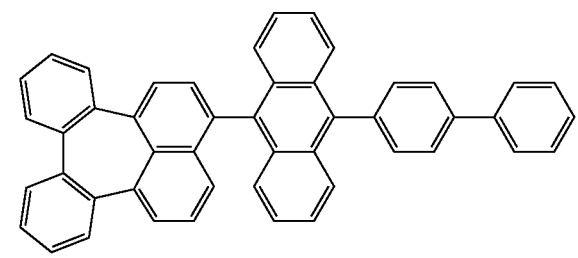

C-3
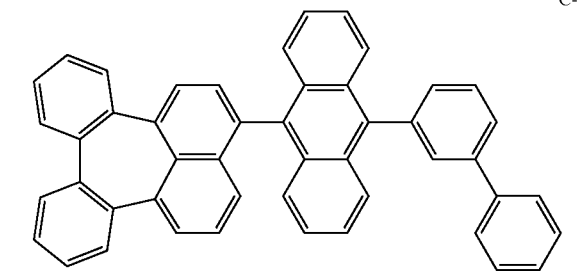

C-4
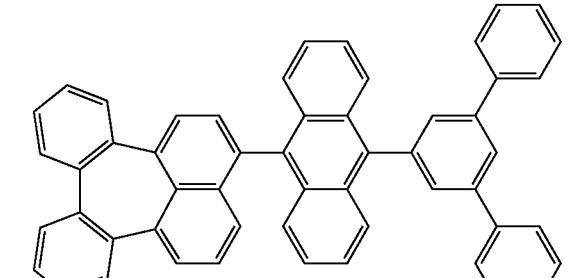

C-5
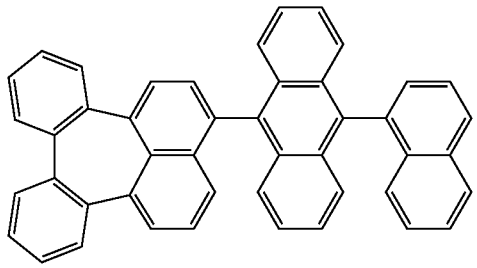

C-6
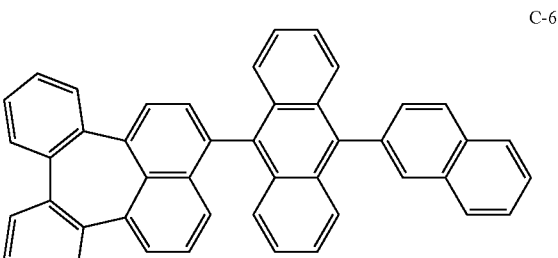

C-7
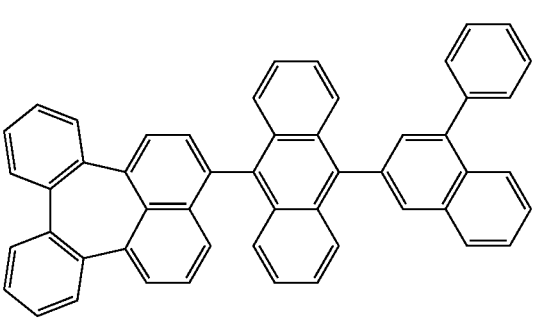

C-8
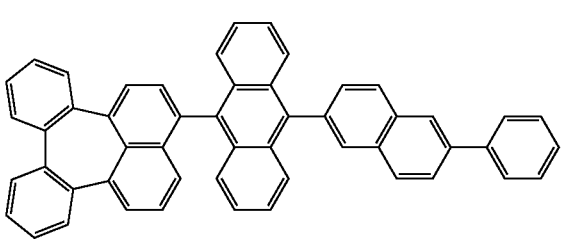

C-9
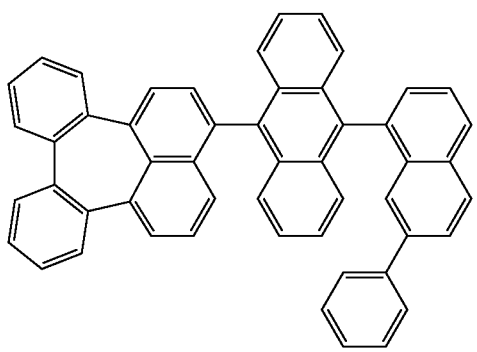

-continued
C-10
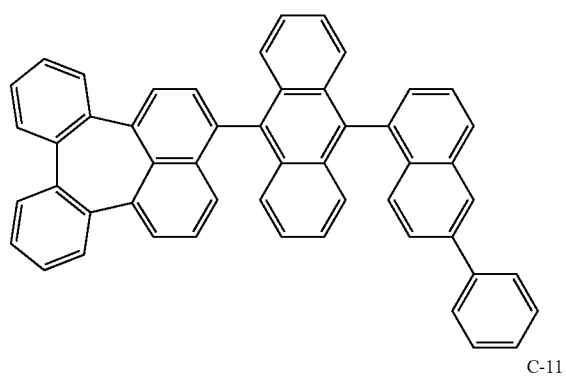
C-11
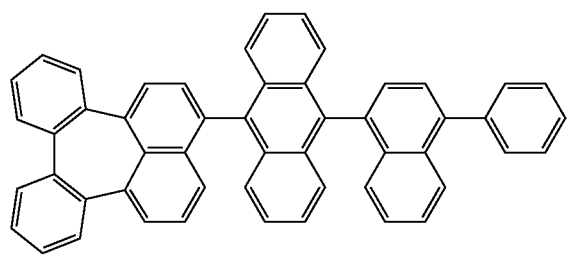
C-12
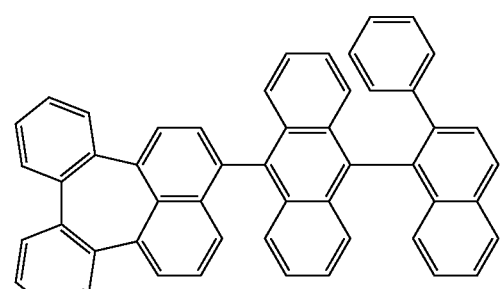
C-13
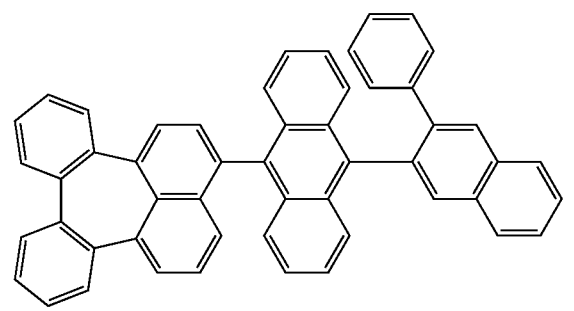
C-14
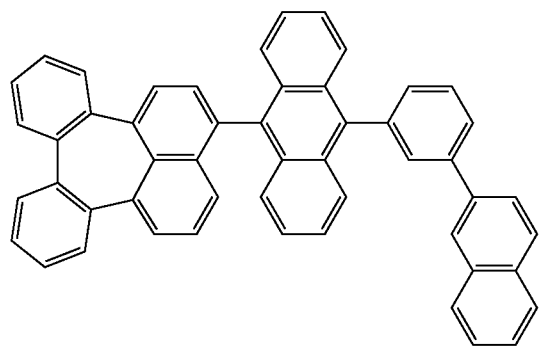
-continued
C-15
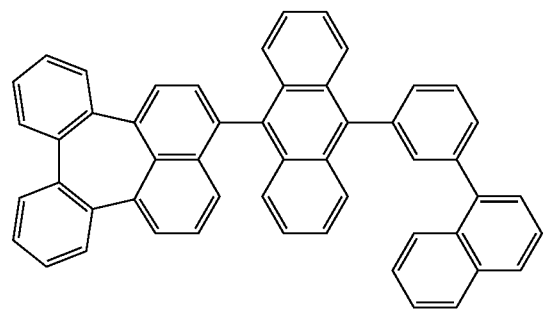
C-16
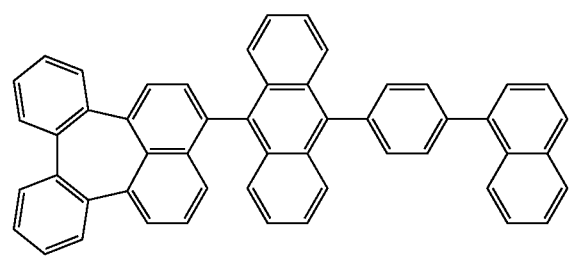
C-17
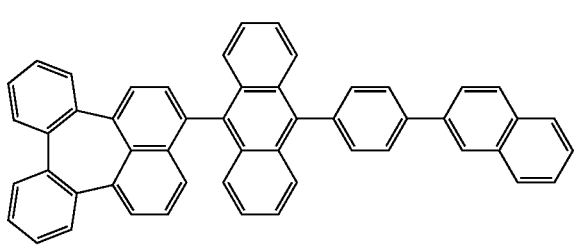
C-18
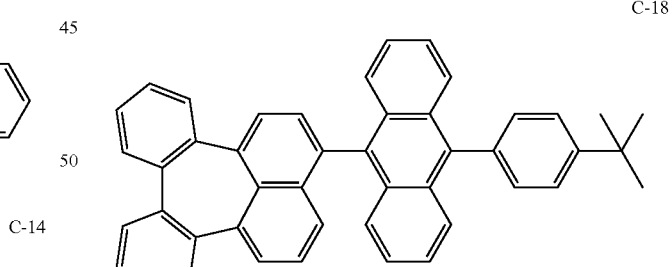
C-19
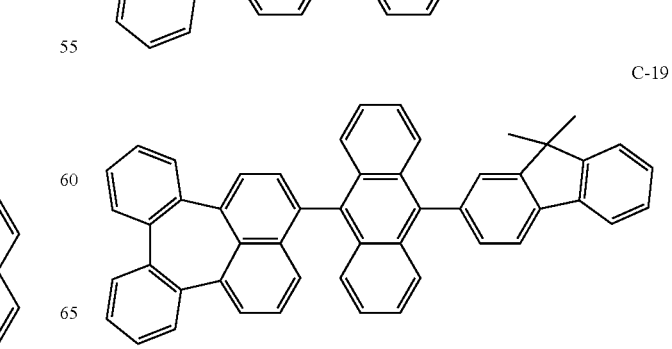

C-20
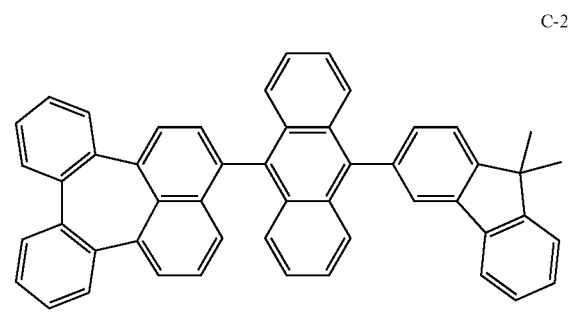
C-25
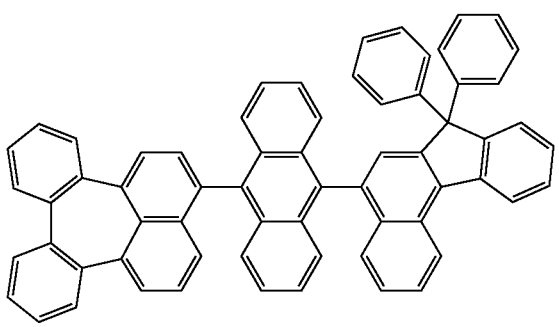
C-21
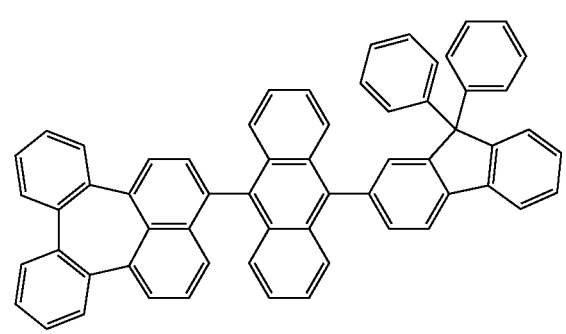
C-26
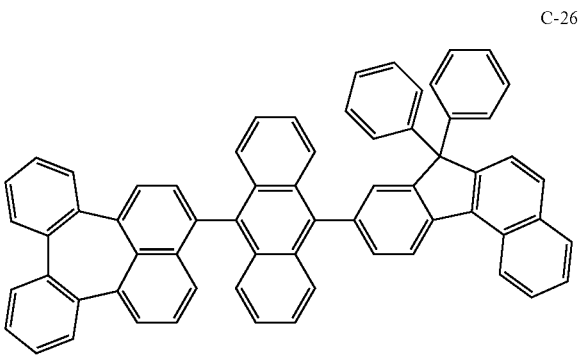
C-22
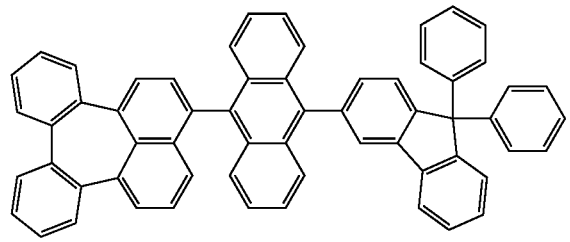
C-27
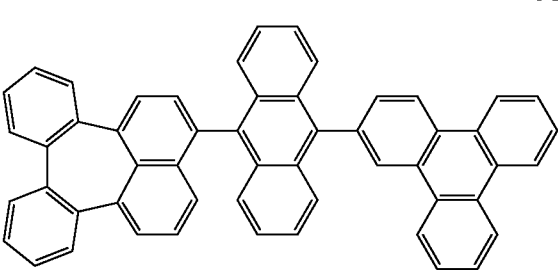
C-23
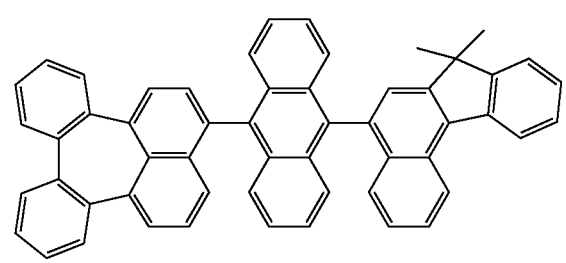
C-28
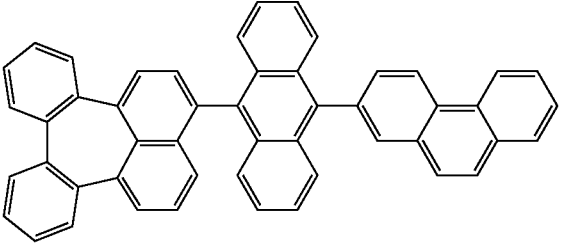
C-24
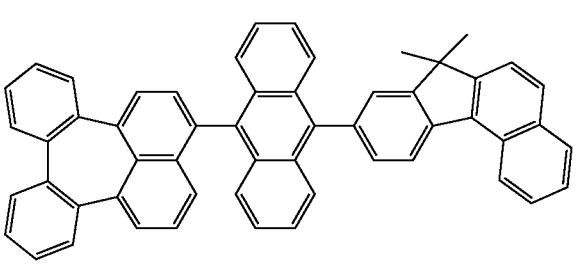
C-29
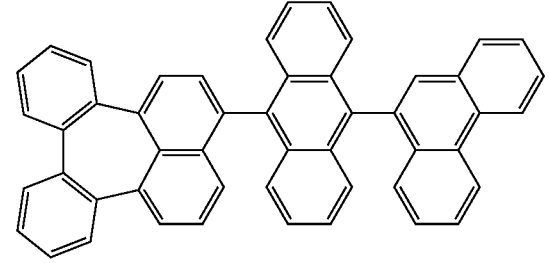

C-30
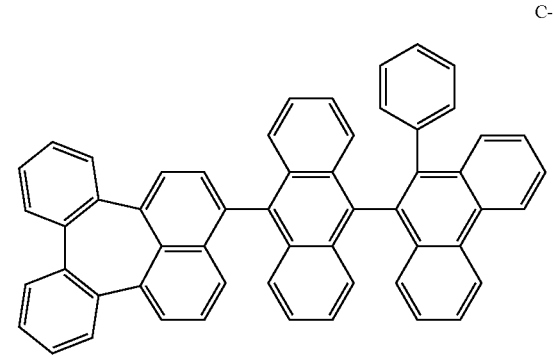
C-31
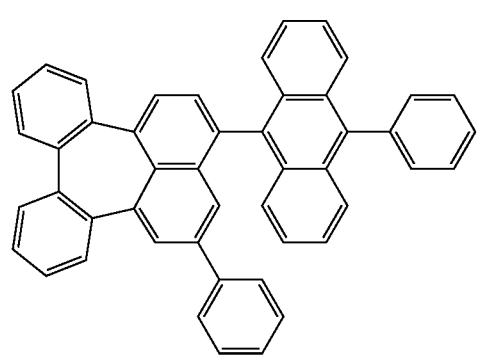
C-32
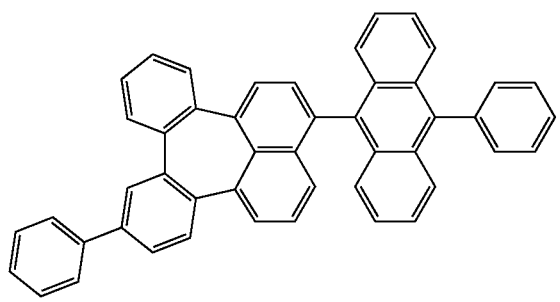
C-33
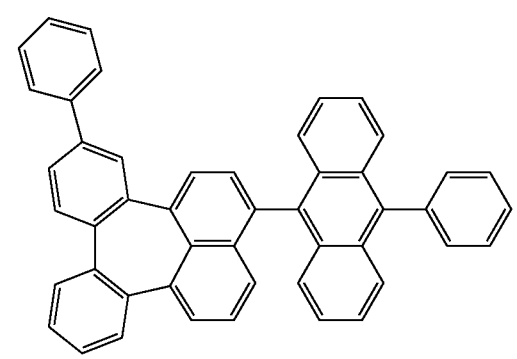
C-34
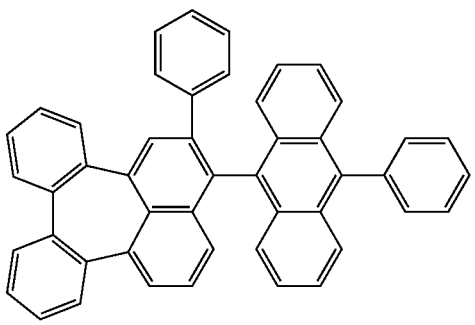
C-35
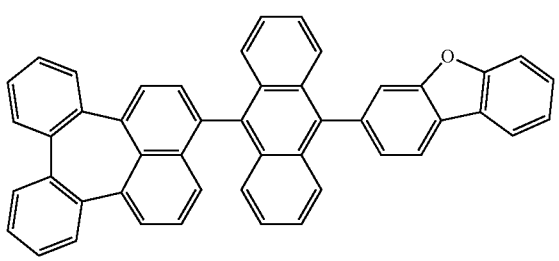
C-36
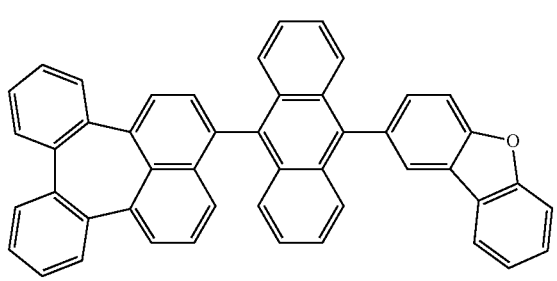
C-37
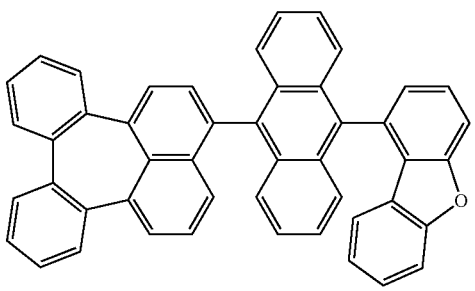
C-38
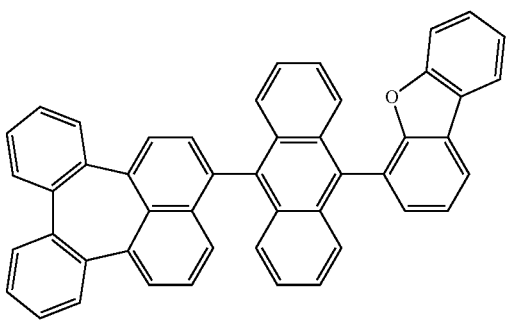

C-39
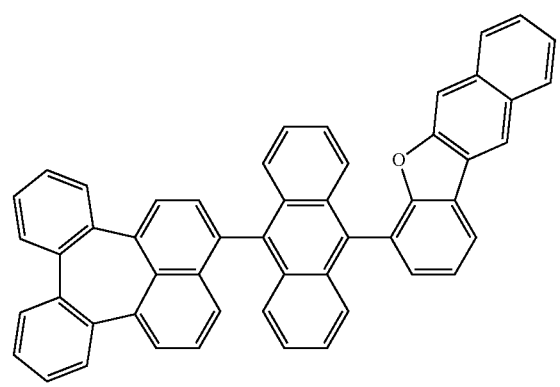
C-40
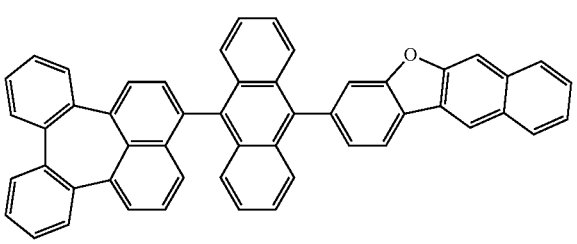
C-41
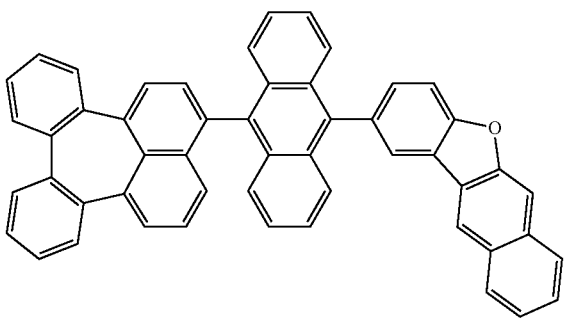
C-42
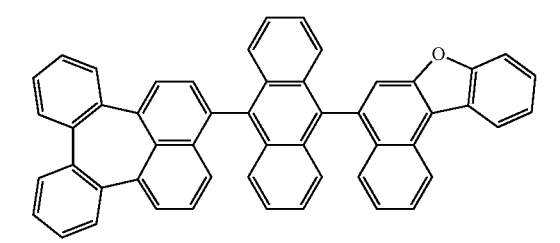
C-43
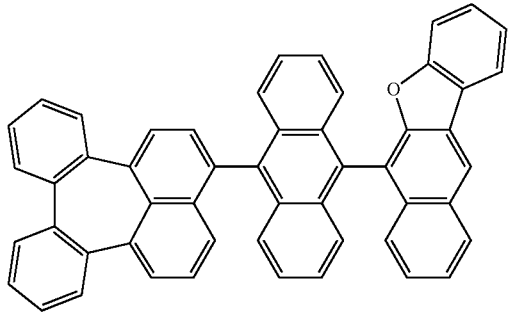
C-44
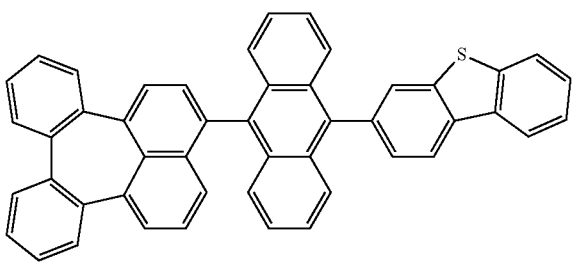
C-45
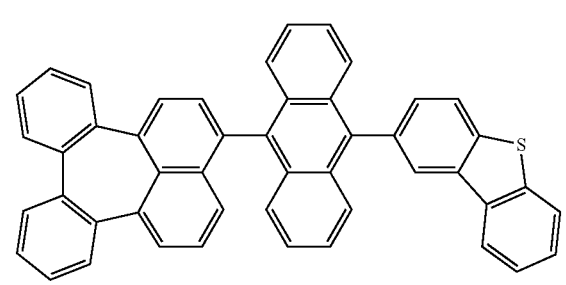
C-46
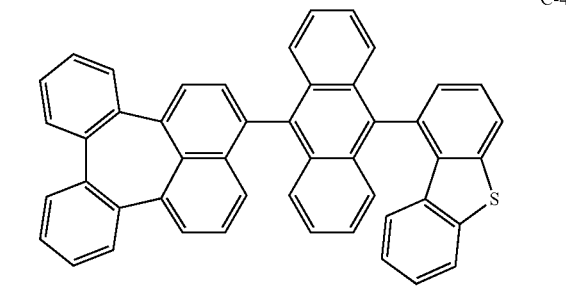
C-47
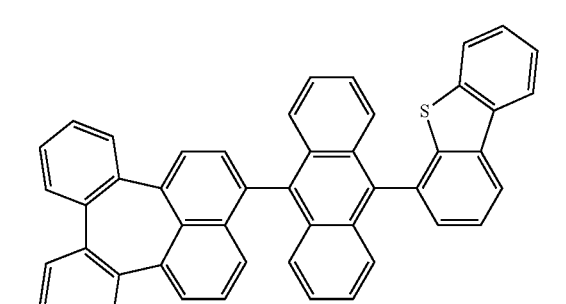
C-48
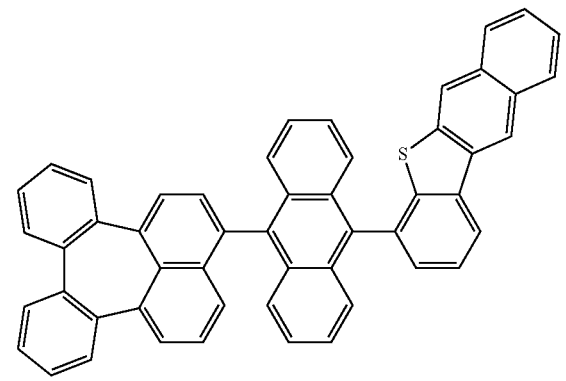

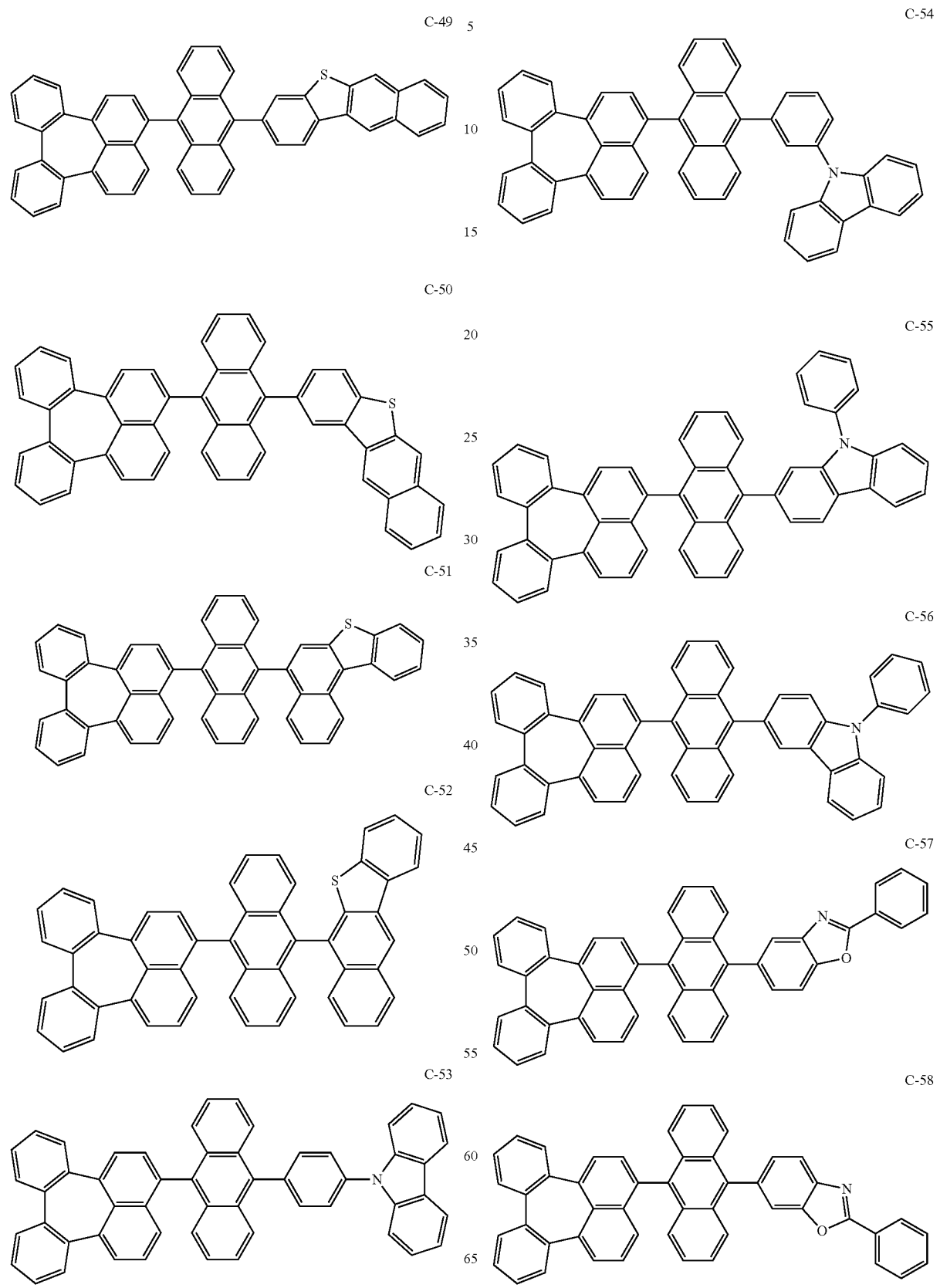

-continued
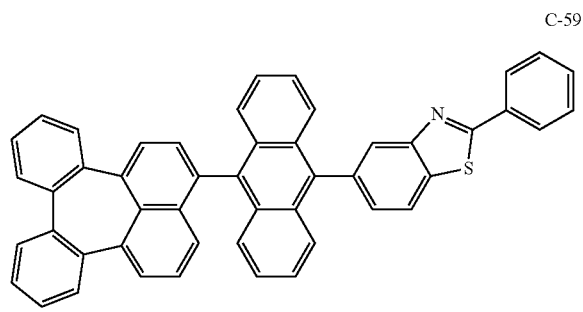
C-59
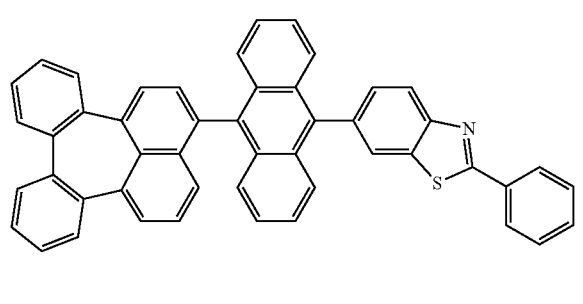
C-60
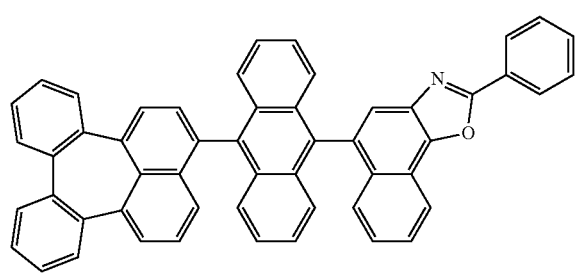
C-61
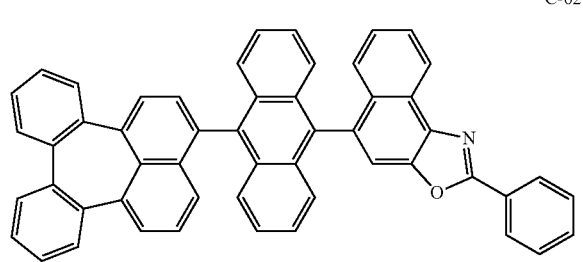
C-62
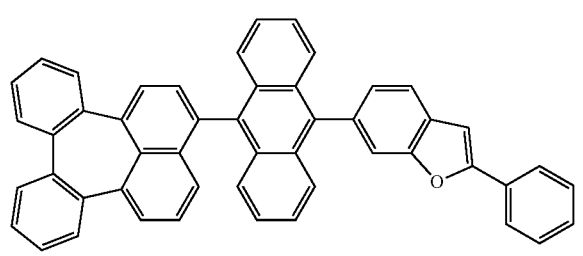
C-63
-continued
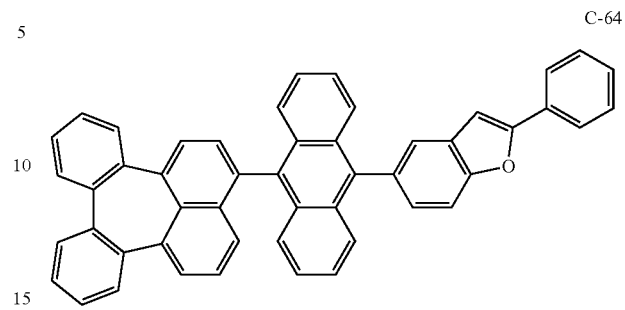
C-64
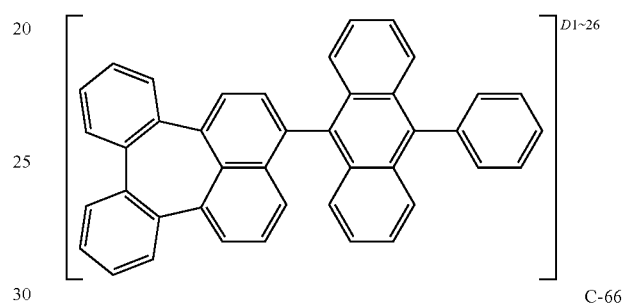
C-65 [D1~26]
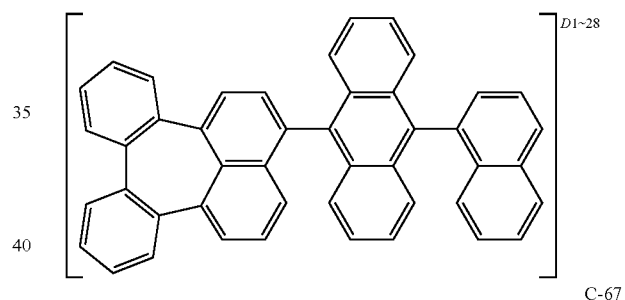
C-66 [D1~28]
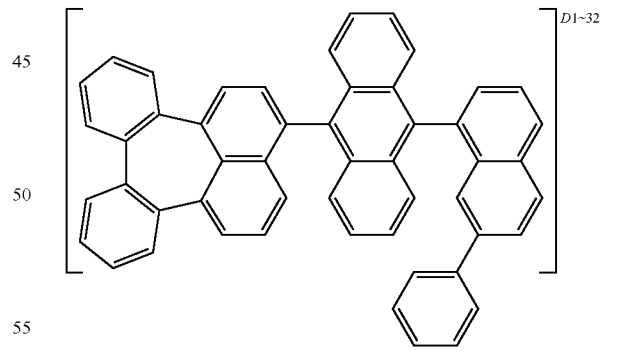
C-67 [D1~32]
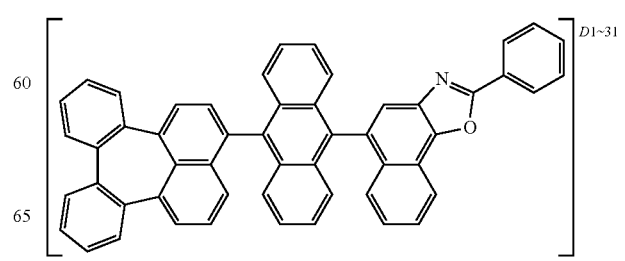
C-68 [D1~31]

C-69
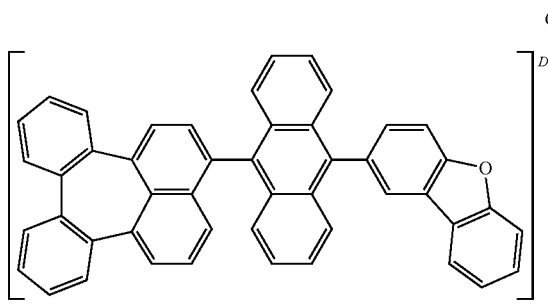
C-74
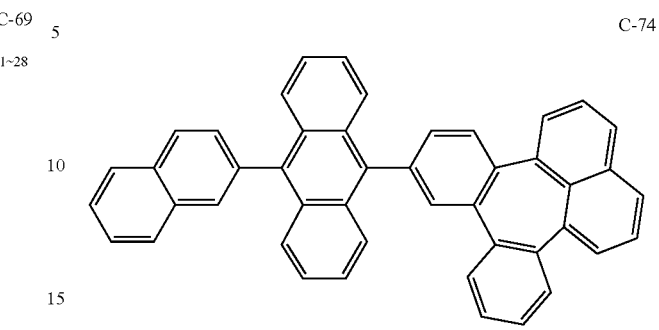
C-70
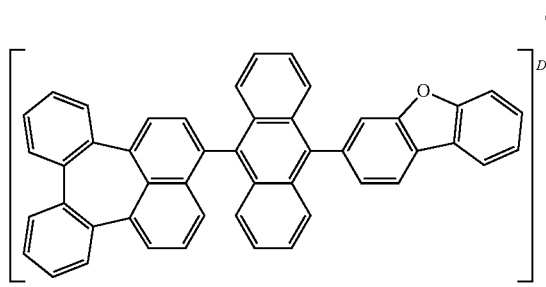
C-75
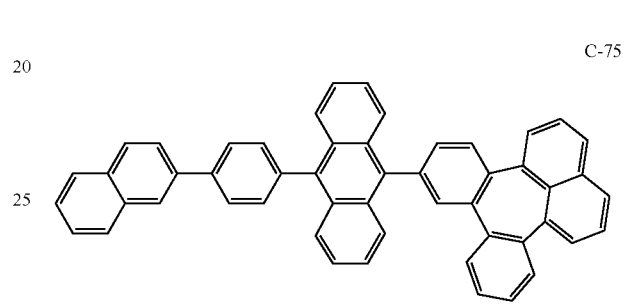
C-71
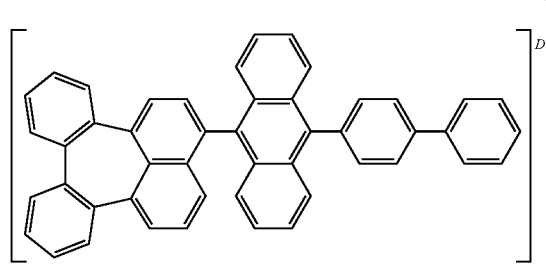
C-76
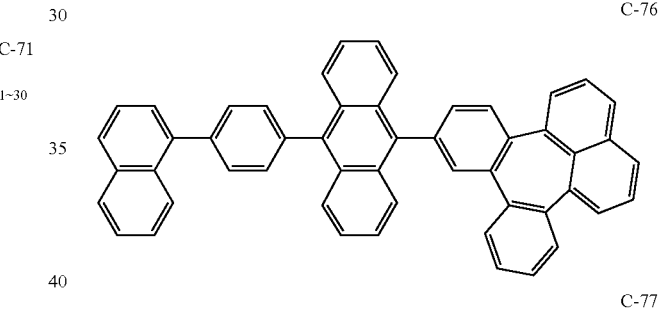
C-72
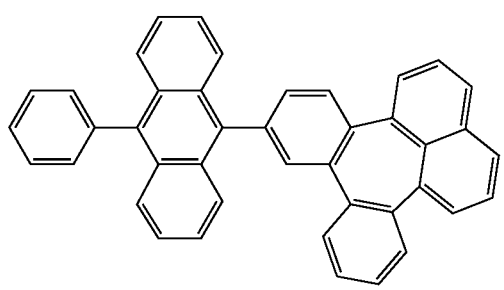
C-77
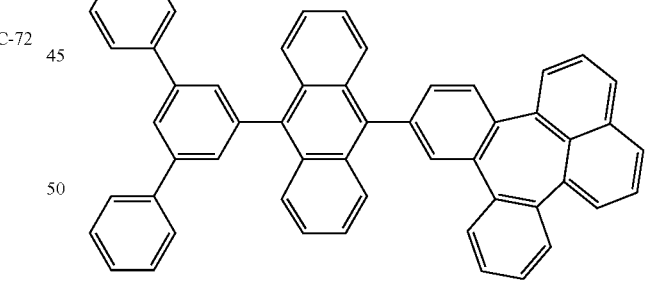
C-73
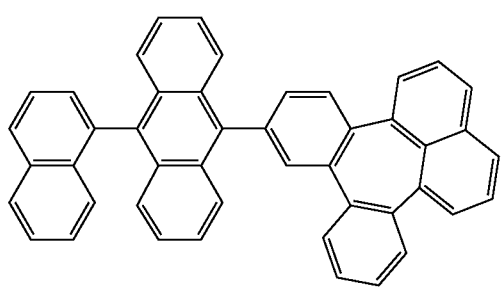
C-78
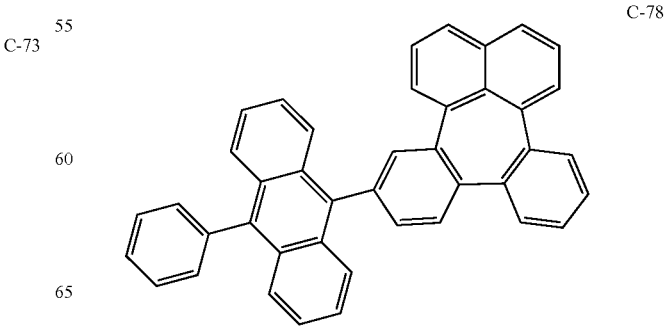

C-79
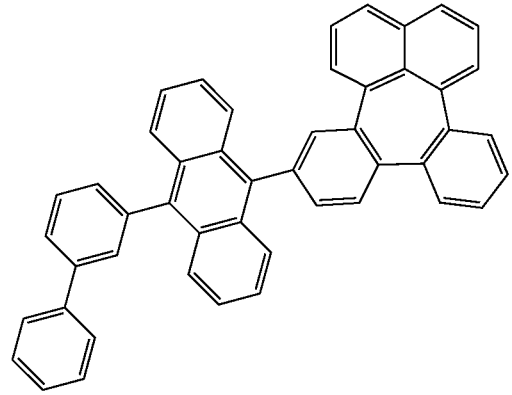
C-80
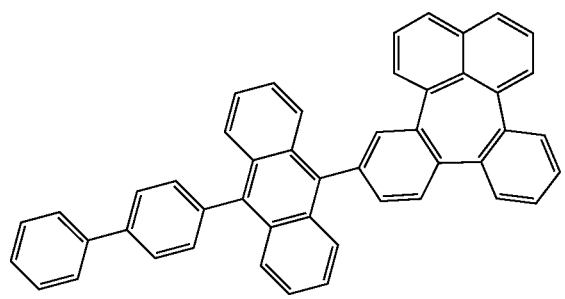
C-81
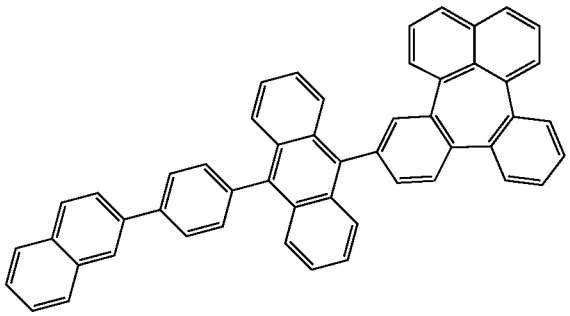
C-82
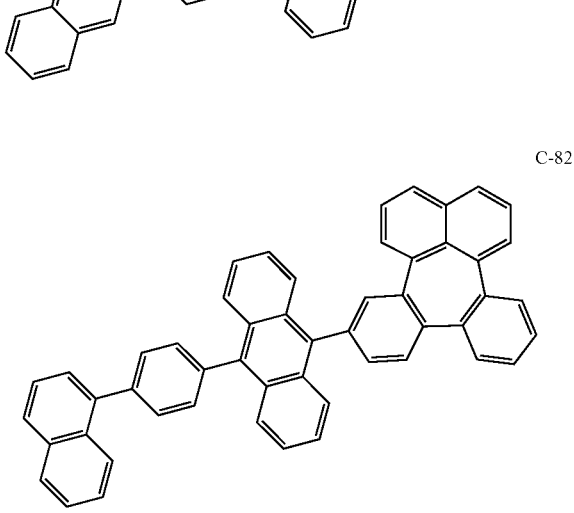
C-83
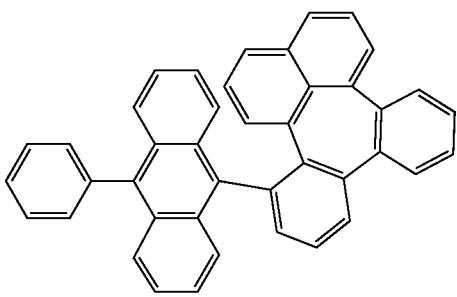
C-84
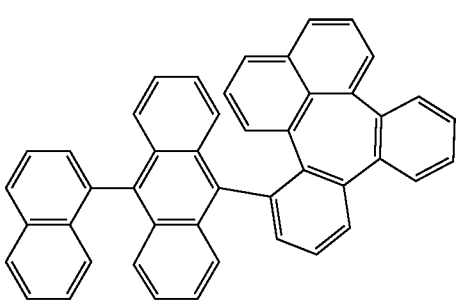
C-85
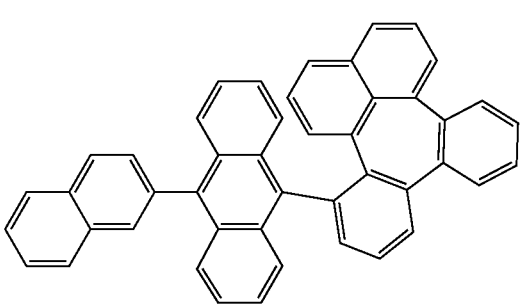
C-86
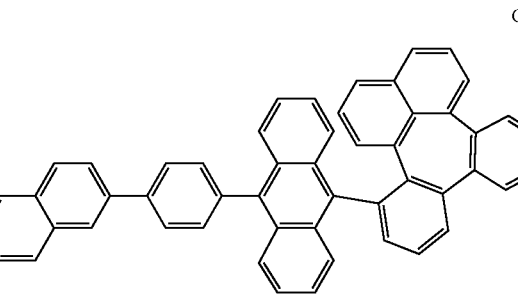
C-87
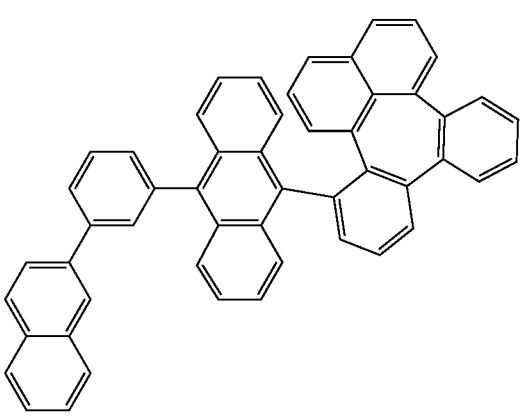

C-88
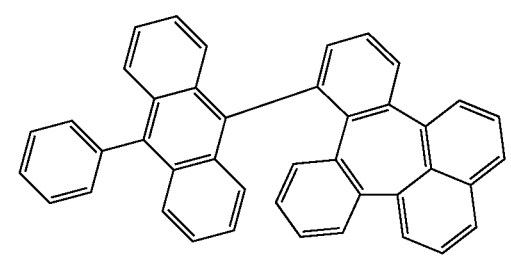
C-89
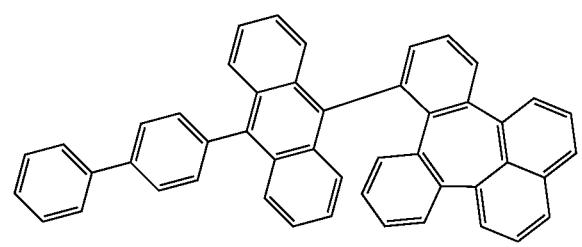
C-90
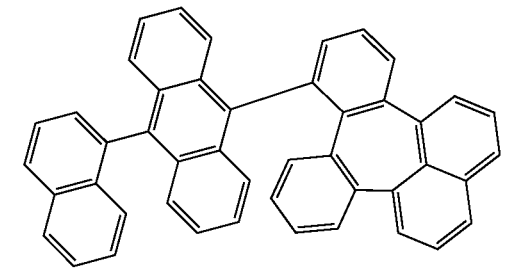
C-91
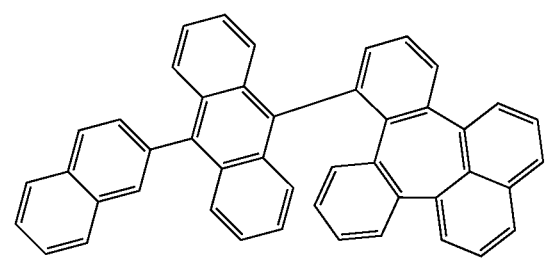
C-92
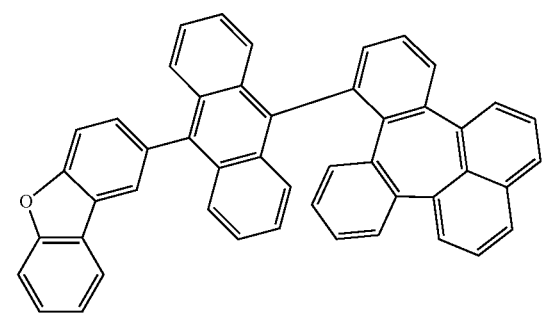
C-93
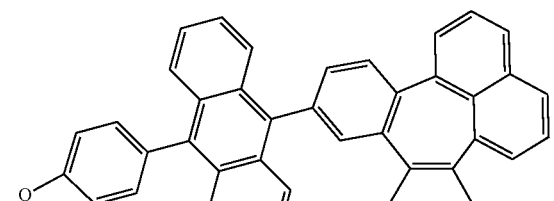
C-94
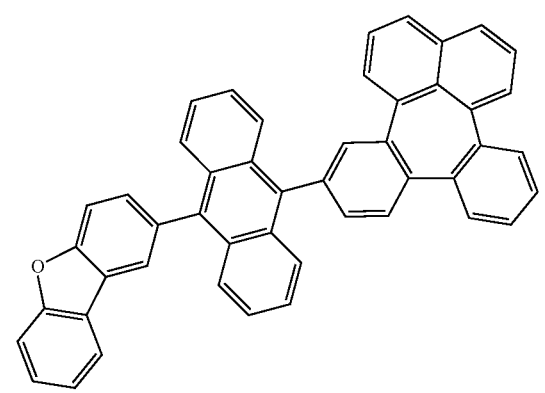
C-95
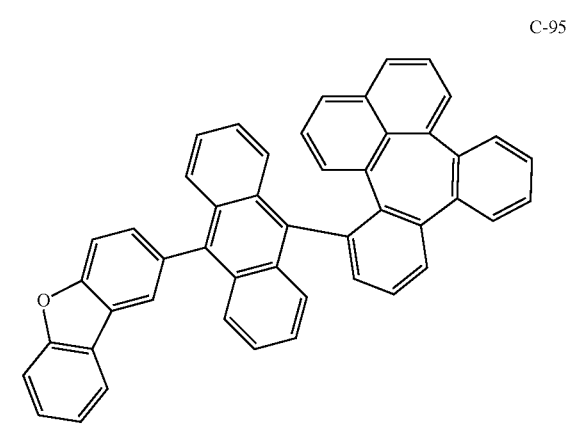
C-96
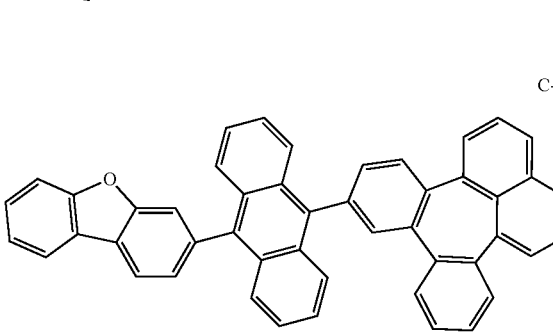

-continued

C-97

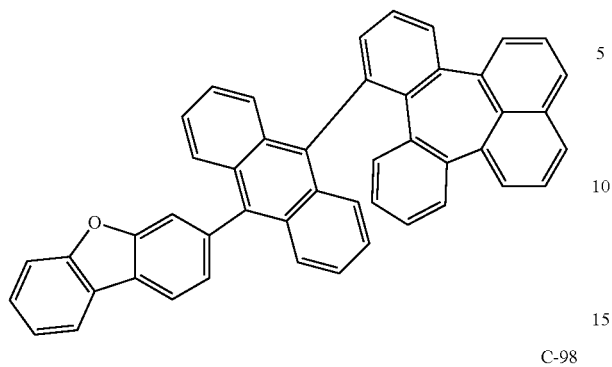

C-98

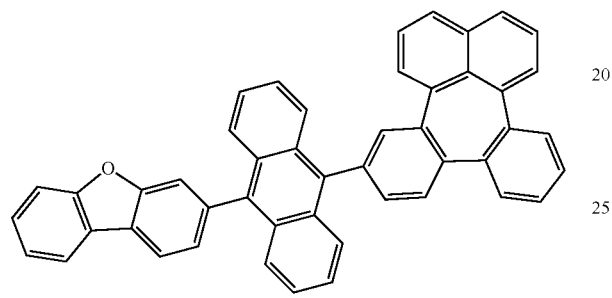

In the formulas, $D_n$ means that n hydrogens in formula 1 are replaced with deuterium. For example, in compound C-65, it means that 1 to 26 hydrogen atoms bonded to carbon atoms of the compound are substituted with deuterium.

The compound of formula 1 according to the present disclosure may be prepared by a synthetic method known to one skilled in the art, and for example, as shown in the following reaction schemes 1 and 2, but is not limited thereto.

[Reaction Scheme 1]

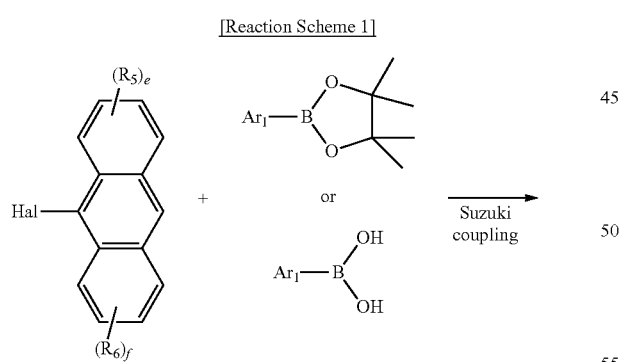

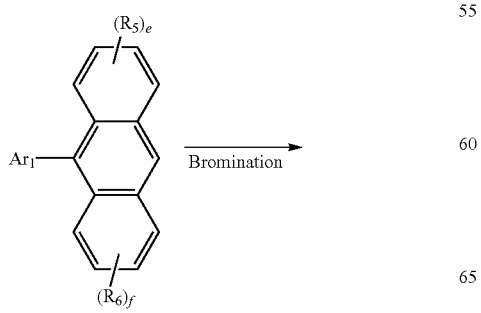

-continued

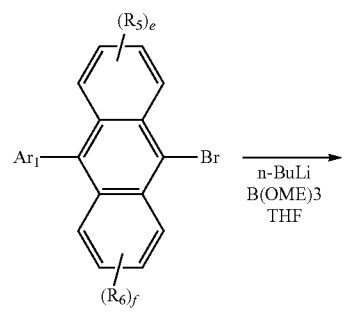

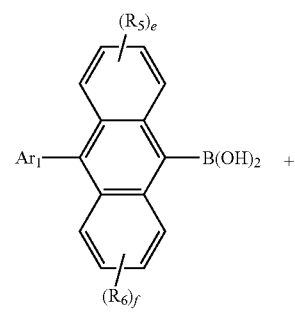

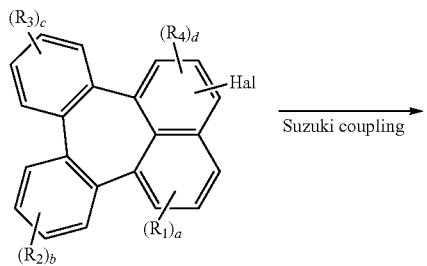

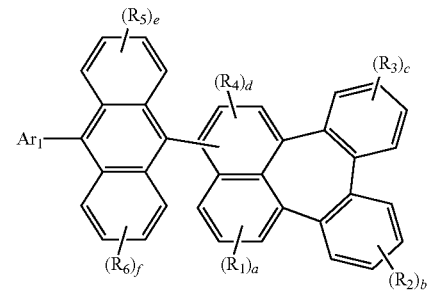

[Reaction Scheme 2]

-continued

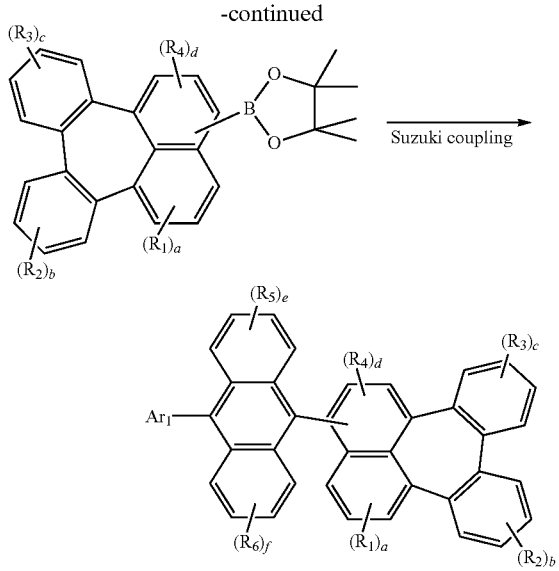

Suzuki coupling

In reaction schemes 1 and 2, $Ar_1$, $R_1$ to $R_6$, and a to f are as defined in formula 1, and Hal represents a halogen.

In addition, the non-deuterated derivative of the compound represented by formula 1 may be prepared by a known coupling or substitution reaction. The deuterated derivative may be prepared by a similar method using a deuterated precursor material, or more generally, treating a non-deuterated compound with D6-benzene in the presence of a Lewis acid such as aluminum trichloride or ethyl aluminum chloride, a H/D exchange catalyst such as trifluoromethanesulfonic acid or trifluoromethanesulfonic acid-D, etc. Further, the degree of deuteration may be controlled by varying reaction conditions such as reaction temperature.

Although illustrative synthesis examples of the compound represented by formula 1 were described above, one skilled in the art will be able to readily understand that all of them are based on a Buchwald-Hartwig cross-coupling reaction, an N-arylation reaction, an H-mont-mediated etherification reaction, a Miyaura borylation reaction, a Suzuki cross-coupling reaction, an Intramolecular acid-induced cyclization reaction, a Pd(II)-catalyzed oxidative cyclization reaction, a Grignard reaction, a Heck reaction, a Cyclic Dehydration reaction, an $SN_1$ substitution reaction, an $SN_2$ substitution reaction, a Phosphine-mediated reductive cyclization reaction, etc., and the above reactions proceed even when substituents which are defined in formula 1 above but are not specified in the specific synthesis examples, are bonded.

The present disclosure provides an organic electroluminescent material comprising the organic electroluminescent compound represented by formula 1, and an organic electroluminescent device comprising the organic electroluminescent material. The material may consist of the organic electroluminescent compound according to the present disclosure alone, or may further comprise conventional materials included in the organic electroluminescent material.

The organic electroluminescent device according to the present disclosure comprises a first electrode, a second electrode, and at least one organic layer between the first and second electrodes, in which the organic layer may comprise at least one organic electroluminescent compound represented by formula 1.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer.

The second electrode may be a transflective electrode or a reflective electrode, and the organic electroluminescent device may be a top emission type, a bottom emission type, or both-sides emission type according to the kinds of the material formed.

The first electrode and the second electrode may each be formed with a transmissive conductive material, a transflective conductive material, or a reflective conductive material.

The organic electroluminescent device may be a top emission type, a bottom emission type, or both-sides emission type according to the kinds of the material forming the first electrode and the second electrode. In addition, the hole injection layer may be further doped with a p-dopant, and the electron injection layer may be further doped with an n-dopant.

The organic electroluminescent compound represented by formula 1 of the present disclosure may be comprised in at least one of a light-emitting layer, a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer, preferably, may be comprised in a light-emitting layer. When used in the light-emitting layer, the organic electroluminescent compound represented by formula 1 of the present disclosure may be comprised as a host material. Preferably, the light-emitting layer may further comprise at least one dopant. If necessary, the organic electroluminescent compound of the present disclosure may be used as a co-host material. That is, the light-emitting layer may further include a compound other than the organic electroluminescent compound represented by formula 1 of the present disclosure (first host material) as a second host material. The weight ratio between the first host material and the second host material is in the range of 1:99 to 99:1.

The dopant comprised in the organic electroluminescent device of the present disclosure is at least one phosphorescent or fluorescent dopant, preferably at least one fluorescent dopant. The fluorescent dopant material applied to the organic electroluminescent device of the present disclosure is not particularly limited.

As a dopant comprised in the organic electroluminescent device of the present disclosure, for example, a condensed polycyclic amine derivative represented by formula 40 may be exemplified, but is not limited thereto.

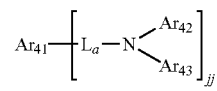

(40)

wherein $Ar_{41}$ represents a substituted or unsubstituted (C6-C50) aryl or styryl; $L_a$ represents a single bond, a substituted or unsubstituted (C6-C30)arylene, or a substituted or unsubstituted (3- to 30-membered)heteroarylene; $Ar_{42}$ and $Ar_{43}$ each independently represent hydrogen, deuterium, a halogen, a substituted or unsubstituted (C1-C30)alkyl, a substituted or unsubstituted (C6-C30)aryl, or a substituted or unsubstituted (3- to 30-membered)heteroaryl; or may be linked to adjacent substituent(s) to form a ring of (3- to 30-membered)monocyclic or polycyclic alicyclic, aromatic or combinations thereof, wherein carbon atoms of the formed alicyclic, aromatic or combinations thereof may be replaced with one or more heteroatoms selected from N, O, and S; jj is 1 or 2, and if jj is 2, each

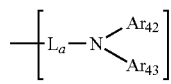

may be the same or different.

Preferred aryl group in $Ar_{41}$ is a substituted or unsubstituted phenyl, a substituted or unsubstituted fluorenyl group, a substituted or unsubstituted anthryl group, a substituted or unsubstituted pyrenyl group, a substituted or unsubstituted chrysenyl group, a substituted or unsubstituted benzofluorenyl group, a spiro[fluorene-benzofluorene], etc.

The organic layer may further comprise at least one compound selected from the group consisting of arylamine-based compounds and styrylarylamine-based compounds.

In addition, in the organic electroluminescent device of the present disclosure, the organic layer may further comprise at least one metal selected from the group consisting of metals of Group 1, metals of Group 2, transition metals of the $4^{th}$ period, transition metals of the $5^{th}$ period, lanthanides and organic metals of d-transition elements of the Periodic Table, or at least one complex compound comprising said metal.

The organic electroluminescent device of the present disclosure may emit white light by further including at least one light-emitting layer containing a blue, red, or green light-emitting compound, which is known in the art, besides the organic electroluminescent compound of the present disclosure. In addition, it may further include a yellow or orange light-emitting layer, if necessary.

In the organic electroluminescent device of the present disclosure, at least one layer selected from a chalcogenide layer, a metal halide layer and a metal oxide layer (hereinafter, "a surface layer") may be preferably placed on an inner surface(s) of one or both electrodes.

Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. The surface layer may provide operation stability for the organic electroluminescent device. Preferably, the chalcogenide includes $SiO_x$ ($1 \leq X \leq 2$), $AlO_x$ ($1 \leq X \leq 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer, a hole transport layer, or an electron blocking layer, or a combination thereof may be used between the anode and the light-emitting layer. The hole injection layer may be multilayers in order to lower the hole injection barrier (or hole injection voltage) from the anode to the hole transport layer or the electron blocking layer, wherein each of the multilayers may use two compounds simultaneously. The hole transport layer or the electron blocking layer may also be multilayers.

An electron buffer layer, a hole blocking layer, an electron transport layer, or an electron injection layer, or a combination thereof can be used between the light-emitting layer and the cathode. The electron buffer layer may be multilayers in order to control the injection of the electron and improve the interfacial properties between the light-emitting layer and the electron injection layer, wherein each of the multilayers may use two compounds simultaneously. The hole blocking layer or the electron transport layer may also be multilayers, wherein each of the multilayers may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. In addition, the hole auxiliary layer may be placed between the hole transport layer (or hole injection layer) and the light-emitting layer, and may be effective to promote or block the hole transport rate (or the hole injection rate), thereby enabling the charge balance to be controlled. Further, the electron blocking layer may be placed between the hole transport layer (or hole injection layer) and the light-emitting layer, and may block overflowing electrons from the light-emitting layer and confine the excitons in the light-emitting layer to prevent light leakage. When an organic electroluminescent device includes two or more hole transport layers, the hole transport layer, which is further included, may be used as a hole auxiliary layer or an electron blocking layer. The hole auxiliary layer and the electron blocking layer may have an effect of improving the efficiency and/or the lifespan of the organic electroluminescent device.

In the organic electroluminescent device of the present disclosure, a mixed region of an electron transport compound and a reductive dopant, or a mixed region of a hole transport compound and an oxidative dopant is preferably placed on at least one surface of a pair of electrodes. In this case, the electron transport compound is reduced to an anion, and thus it becomes easier to inject and transport electrons from the mixed region to an electroluminescent medium. Further, the hole transport compound is oxidized to a cation, and thus it becomes easier to inject and transport holes from the mixed region to the electroluminescent medium. Preferably, the oxidative dopant includes various Lewis acids and acceptor compounds; and the reductive dopant includes alkali metals, alkali metal compounds, alkaline earth metals, rare-earth metals, and mixtures thereof. A reductive dopant layer may be employed as a charge-generating layer to prepare an organic electroluminescent device having two or more light-emitting layers, which emits white light.

An organic electroluminescent material according to one embodiment of the present disclosure may be used as light-emitting materials for a white organic light-emitting device. The white organic light-emitting device has been suggested in various structures such as a parallel side-by-side arrangement method, a stacking arrangement method, or CCM (color conversion material) method, etc., according to the arrangement of R (Red), G (Green), B (blue), or YG (yellowish green) light-emitting units. In addition, the organic electroluminescent material according to one embodiment of the present disclosure may also be applied to the organic electroluminescent device comprising a QD (quantum dot).

In order to form each layer of the organic electroluminescent device of the present disclosure, dry film-forming methods such as vacuum evaporation, sputtering, plasma, ion plating, etc., or wet film-forming methods such as spin coating, ink jet printing, dip coating, flow coating, etc., can be used.

When using a wet film-forming method, a thin film can be formed by dissolving or diffusing the materials forming each layer into any suitable solvent such as ethanol, chloroform, tetrahydrofuran, dioxane, etc. The solvent is not specifically limited as long as the material forming each layer is soluble or dispersible in the solvents, which do not cause any problems in forming a film.

It is possible to produce a display system, e.g., a display system for smartphones, tablets, notebooks, PCs, TVs, or cars, or a lighting system, e.g., an outdoor or indoor lighting system, by using the organic electroluminescent device of the present disclosure.

Hereinafter, the preparation method of the compound of the present disclosure, and the properties thereof, and the luminous property of the organic electroluminescent device comprising the same will be explained in detail with reference to the representative compounds of the present disclosure. However, the present disclosure is not limited to the following examples.

Example 1: Preparation of Compound C-1

Compound A-1 (10.5 g, 0.029 mol), compound A-2 (8.9 g, 0.032 mol), Pd(OAc)$_2$ (0.33 g, 0.001 mol), s-phos (1.2 g, 0.002 mmol), K$_2$CO$_3$ (12.1 g, 0.088 mol), 26 mL of acetonitrile, 52 mL of distilled water, and 126 mL of toluene were added to a flask and stirred at 120° C. for 16 hours. The mixture was cooled to room temperature, extracted with ethyl acetate (EA), and the organic layer was washed with distilled water. The obtained organic layer was distilled under reduced pressure and separated by column chromatography to obtain compound C-1 (4 g, 26.5%).

|  | MW | M.P. |
|---|---|---|
| C-1 | 530.20 | 394° C. |

Example 2: Preparation of Compound C-35

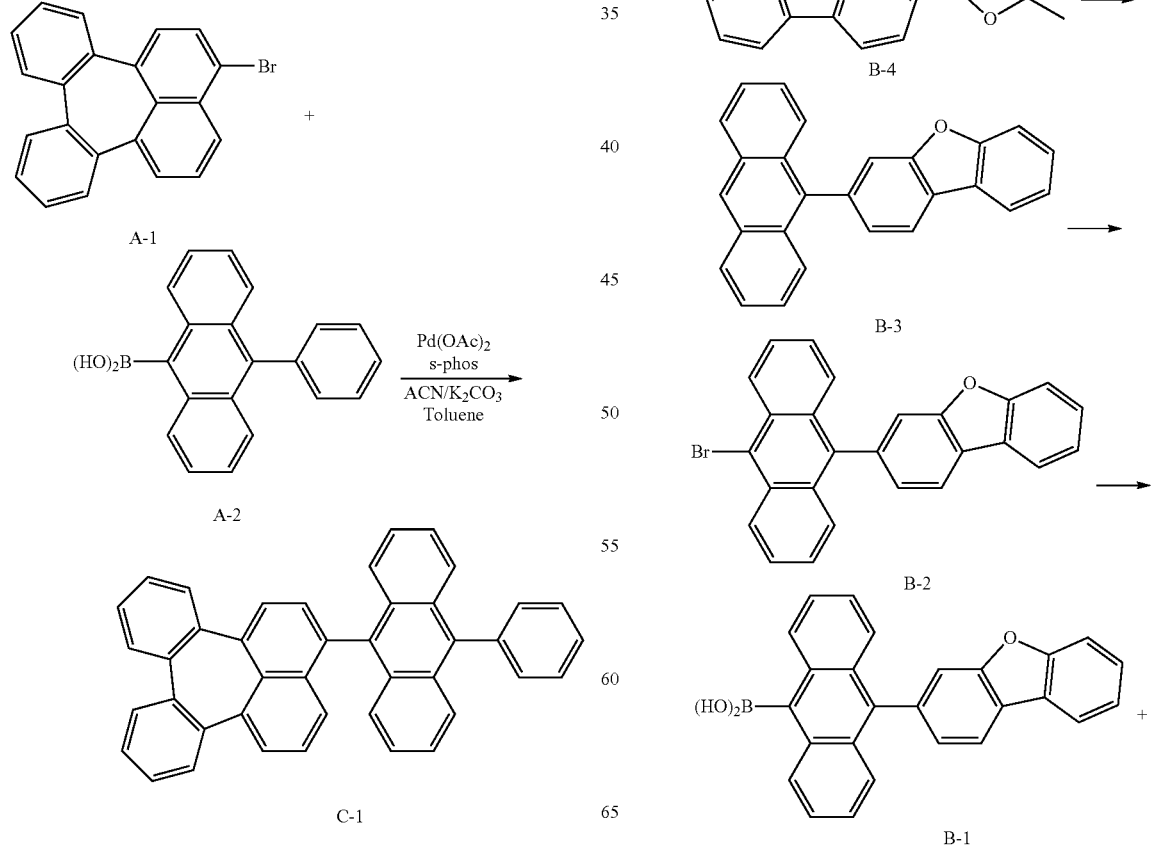

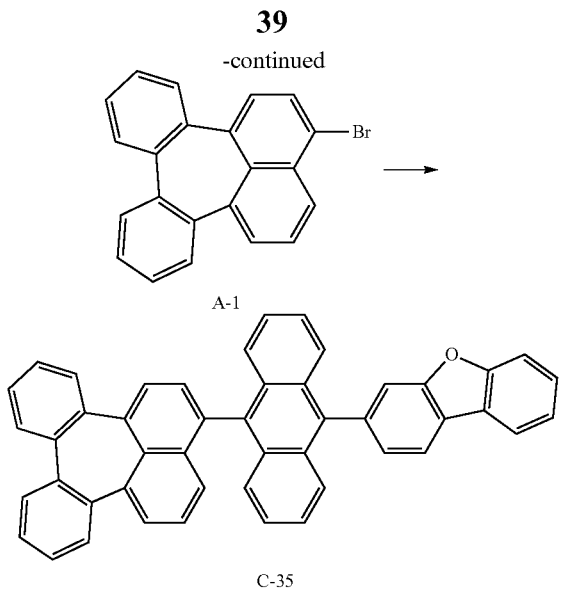

1) Preparation of Compound B-3

Compound 9-bromoanthracene (20 g, 0.077 mol), compound B-4 (25.1 g, 0.085 mol), Pd(PPh$_3$)$_4$ (4.5 g, 0.003 mol), K$_2$CO$_3$ (32 g, 0.23 mol), 97 mL of ethanol, 97 mL of distilled water, and 390 mL of toluene were added to a flask and stirred at 100° C. After 12 hours, the mixture was cooled to room temperature, extracted with dichloromethane, and the organic layer was washed with distilled water. The obtained organic layer was distilled under reduced pressure and separated by column chromatography to obtain compound B-3 (25.8 g, 96.6%).

2) Preparation of Compound B-2

Compound B-3 (25.8 g, 0.074 mol) was added to a flask, dissolved in 374 mL of dimethylformamide (DMF), and N-bromosuccinimide (13.3 g, 0.074 mol) was added thereto. The mixture was stirred at room temperature for 18 hours, extracted with dichloromethane, and the organic layer was washed with distilled water. The obtained organic layer was distilled under reduced pressure and separated by column chromatography to obtain compound B-2 (30 g, 94.6%).

3) Preparation of Compound B-1

Compound B-2 (30 g, 0.070 mol) was added to a flask, and 700 mL of tetrahydrofuran was added thereto. N-BuLi (37 mL, 2.5 M, 0.092 mol) was slowly added at −78° C. After 10 minutes, trimethylborate (10.3 mL, 0.092 mol) was added thereto. After stirring the mixture for 12 hours, distilled water was added thereto. The organic layer was extracted with ethyl acetate, and the remaining moisture was removed with magnesium sulfate. The organic layer was distilled under reduced pressure, and solidified by adding hexane to obtain compound B-1 (16 g, 58.8%).

4) Preparation of Compound C-35

Compound A-1 (6 g, 0.016 mol), Compound B-1 (8.4 g, 0.021 mol), Pd(PPh$_3$)$_4$ (0.97 g, 0.00084 mol), K$_2$CO$_3$ (6.9 g, 0.050 mol), 20 mL of ethanol, 20 mL of distilled water, and 84 mL of toluene were added to a flask, and the mixture was stirred at 130° C. After 16 hours, the mixture was cooled to room temperature, extracted with ethyl acetate, and the organic layer was washed with distilled water. The obtained organic layer was distilled under reduced pressure and separated by column chromatography to obtain compound C-35 (5.5 g, 52.7%).

|   | MW | M.P. |
|---|---|---|
| C-35 | 620.75 | 347° C. |

Device Example 1: Producing an OLED Comprising a Compound According to the Present Disclosure An OLED using an organic electroluminescent compound according to the present disclosure was produced as follows: A transparent electrode indium tin oxide (ITO) thin film (10 Ω/sq) on a glass substrate for an OLED (GEOMATEC CO., LTD., Japan) was subjected to an ultrasonic washing with acetone, ethanol, and distilled water, sequentially, and then was stored in isopropanol. The ITO substrate was mounted on a substrate holder of a vacuum vapor deposition apparatus. Compound HI-1 was introduced into a cell of the vacuum vapor deposition apparatus, and the pressure in the chamber of the apparatus was then controlled to 10$^{-6}$ torr. Thereafter, an electric current was applied to the cell to evaporate the above-introduced material, thereby forming a first hole injection layer having a thickness of 60 nm on the ITO substrate. Next, compound HI-2 was introduced into another cell of the vacuum vapor deposition apparatus and was evaporated by applying an electric current to the cell, thereby forming a second hole injection layer having a thickness of 5 nm on the first hole injection layer. Compound HT-1 was then introduced into another cell of the vacuum vapor deposition apparatus and was evaporated by applying an electric current to the cell, thereby forming a first hole transport layer having a thickness of 20 nm on the second hole injection layer. Compound HT-2 was then introduced into another cell of the vacuum vapor deposition apparatus and was evaporated by applying an electric current to the cell, thereby forming a second hole transport layer having a thickness of 5 nm on the first hole transport layer. After forming the hole injection layers and the hole transport layers, a light-emitting layer was formed thereon as follows: Compound C-1 was introduced into one cell of the vacuum vapor depositing apparatus as a host of the light-emitting layer, and compound BD was introduced into another cell. The two materials were evaporated at different rates and the dopant was deposited in a doping amount of 2 wt % based on the total amount of the host and dopant to form a light-emitting layer having a thickness of 20 nm on the second hole transport layer. Next, compound ET-1 and compound EI-1 were evaporated at a rate of 1:1 in an amount of 50% by weight, respectively, in two other cells to deposit an electron transport layer having a thickness of 35 nm on the light-emitting layer. After depositing compound EI-1 as an electron injection layer having a thickness of 2 nm on the electron transport layer, an Al cathode having a thickness of 80 nm was deposited on the electron injection layer by another vacuum vapor deposition apparatus. Thus, an OLED was produced.

Device Example 2: Producing an OLED Comprising a Compound According to the Present Disclosure An OLED was produced in the same manner as in Device Example 1, except that compound C-35 instead of compound C-1 was used as the host material of the light-emitting layer.

Comparative Example: Producing an OLED Comprising a Conventional Compound

An OLED was produced in the same manner as in Device Example 1, except that compound BH-1 instead of compound C-1 was used as the host material of the light-emitting layer.

As a result, the measurement results of driving voltage, current efficiency, and electroluminescence wavelength based on 1,000 nit luminance of the organic electroluminescent devices of Device Examples 1 and 2 and Comparative Example are shown in Table 1 below.

TABLE 1

| Host | Driving Voltage (V) | Current Efficiency (cd/A) | Electroluminescence Wavelength |
|---|---|---|---|
| | | @ 1,000 nit | |
| Device Example 1 | C-1 | 3.9 | 9.6 | 459 |
| Device Example 2 | C-35 | 3.8 | 10.0 | 461 |
| Comparative Example | BH-1 | 4.2 | 8.5 | 457 |

From Table 1 above, it can be seen that the organic electroluminescent device comprising the organic electroluminescent compound according to the present disclosure as a host material exhibits a driving voltage equal to or greater when compared to a device using a comparative compound, and significantly improves the current efficiency characteristics.

The compounds used in the Device Examples and Comparative Example are shown in Table 2 below.

TABLE 2

Hole injection layer/ hole transport layer

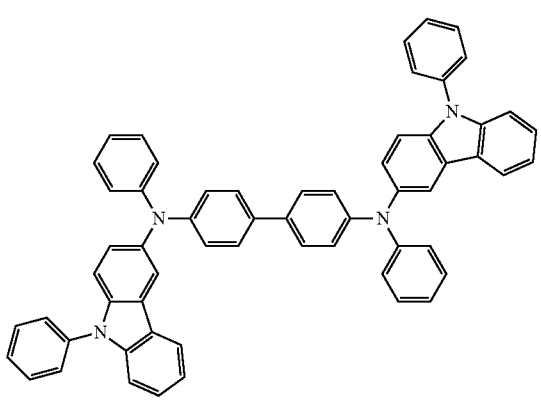

HI-1

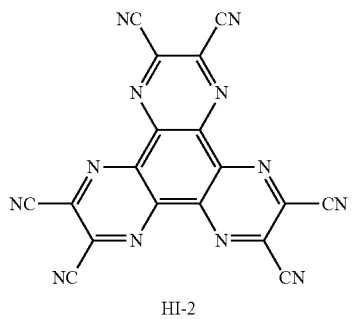

HI-2

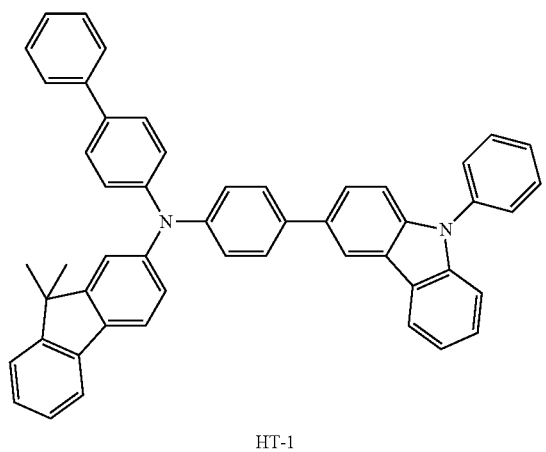

HT-1

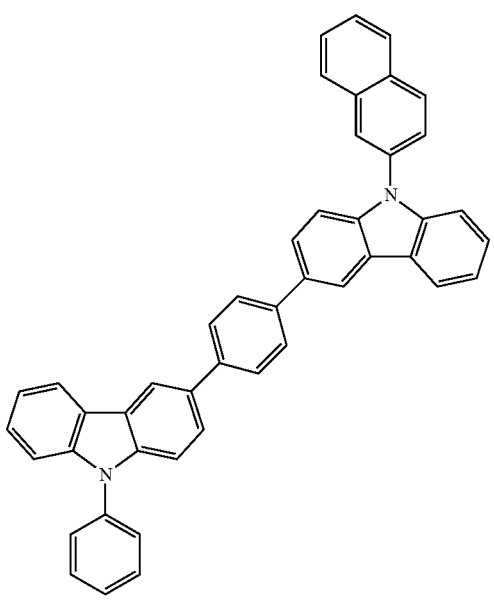

HT-2

TABLE 2-continued
Light-emitting layer
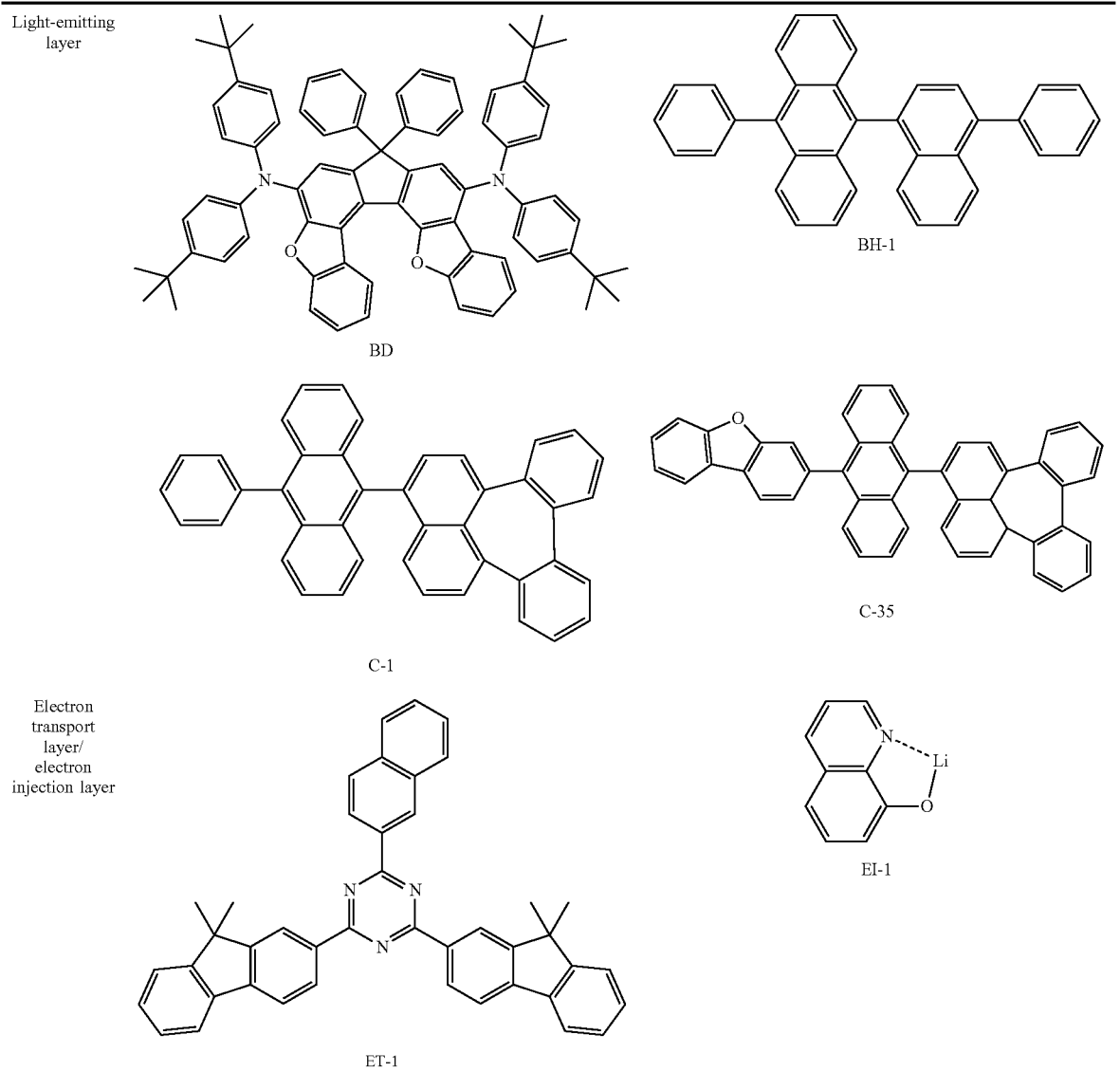
Electron transport layer/ electron injection layer
The invention claimed is:
1. An organic electroluminescent compound represented by the following formula 1-1 or 1-2:
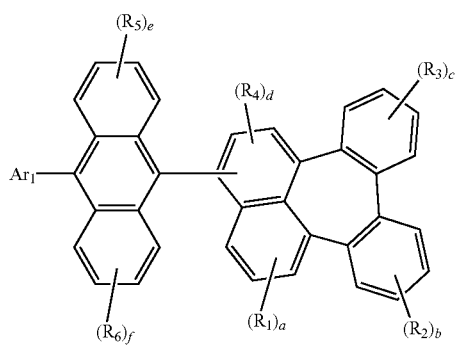
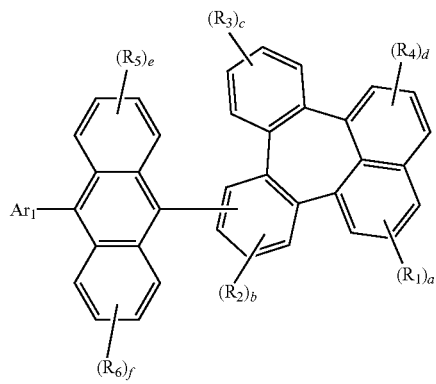
wherein
Ar$_1$ represents a substituted or unsubstituted (C6-C30) aryl;

R₁ to R₄ each independently represent hydrogen, deuterium, a halogen, a cyano, a substituted or unsubstituted (C1-C30)alkyl, a substituted or unsubstituted (C6-C30)aryl, or a substituted or unsubstituted (5- to 30-membered)heteroaryl;

R₅ and R₆ each independently represent hydrogen, deuterium, a halogen, a cyano, a substituted or unsubstituted (C1-C30)alkyl, a substituted or unsubstituted (C6-C30)aryl, or a substituted or unsubstituted (5- to 30-membered)heteroaryl;

a and d each independently represent an integer of 1 to 3, and b, c, e, and f each independently represent an integer of 1 to 4; wherein if a to f are integers of 2 or more, each R₁ to each R₆ may be the same or different from each other, with a proviso that d is 1 or 2 in formula 1-1 and b is 1, 2, or 3 in formula 1-2.

2. The organic electroluminescent compound according to claim 1, wherein the substituents of the substituted alkyl, the substituted aryl, and the substituted heteroaryl in R₁ to R₆, and Ar₁ each independently are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with a (C6-C30)aryl(s); a (C6-C30)aryl unsubstituted or substituted with at least one of deuterium, a (C1-C30)alkyl(s) and a (3- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di- (C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

3. The organic electroluminescent compound according to claim 1, wherein the compound represented by formula 1-1 or 1-2 is selected from the group consisting of the following compounds:

C-1

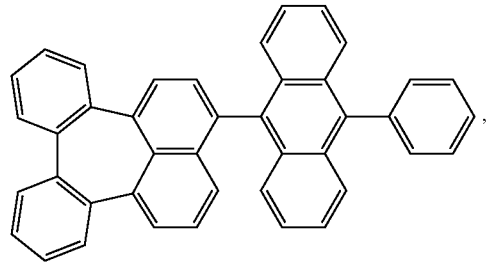

C-2

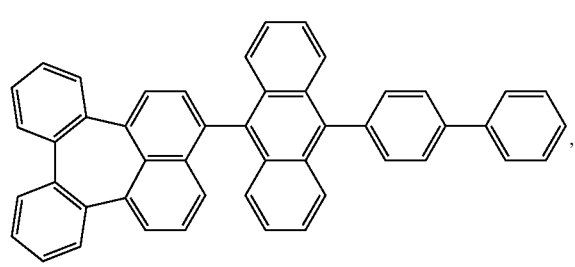

C-3

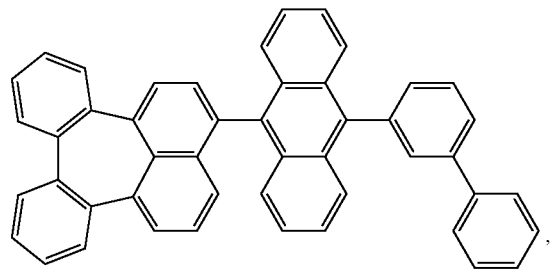

C-4

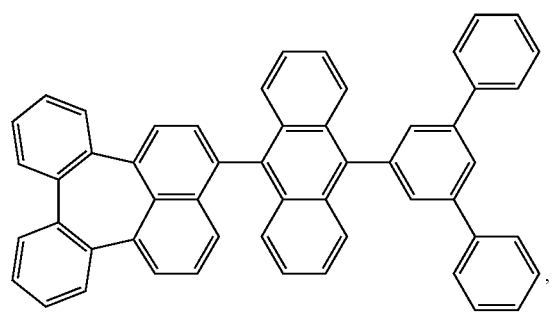

C-5

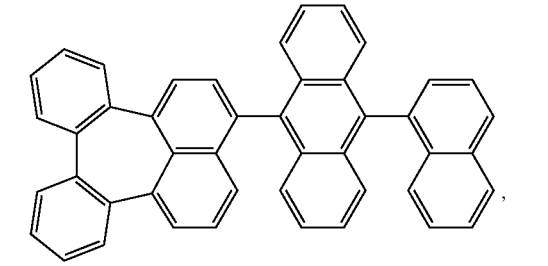

C-6

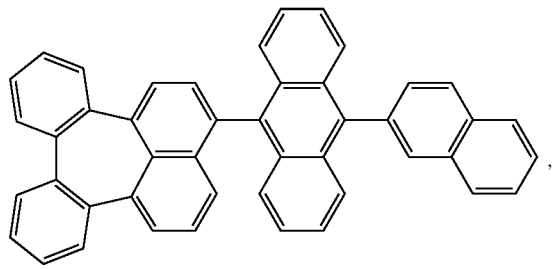

C-7

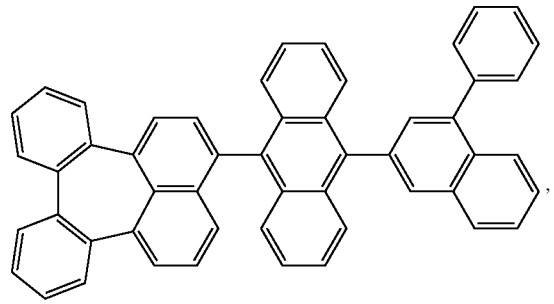

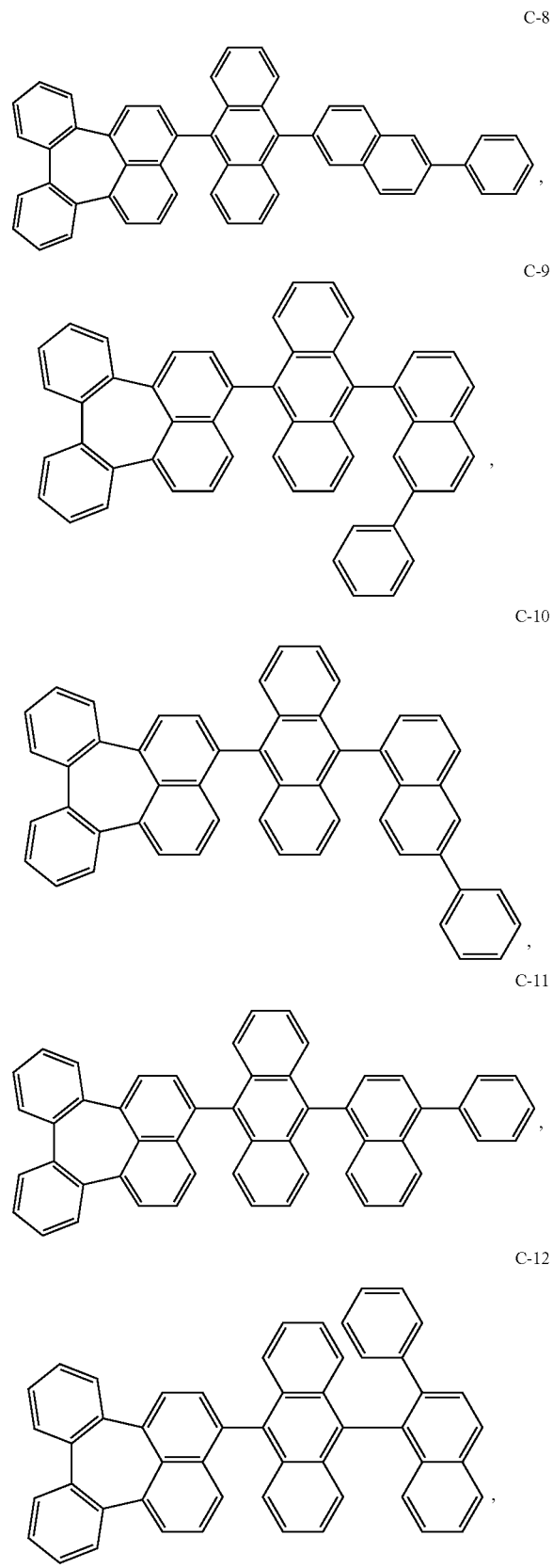
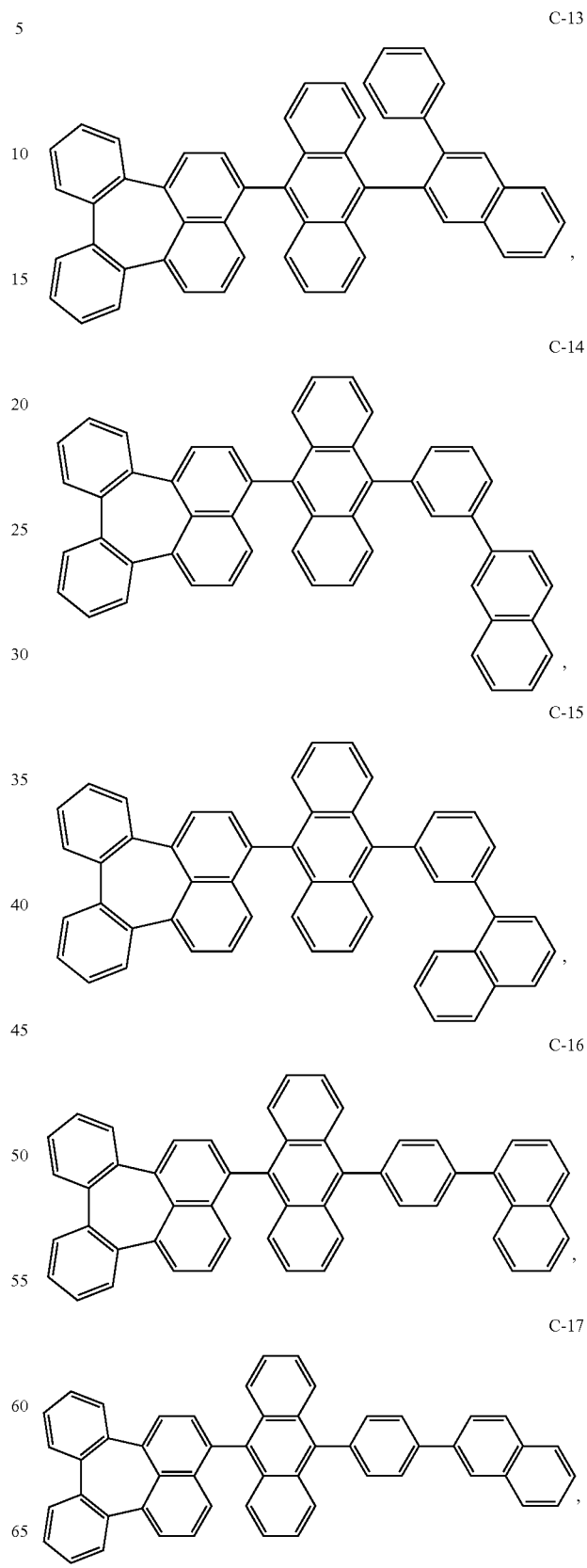

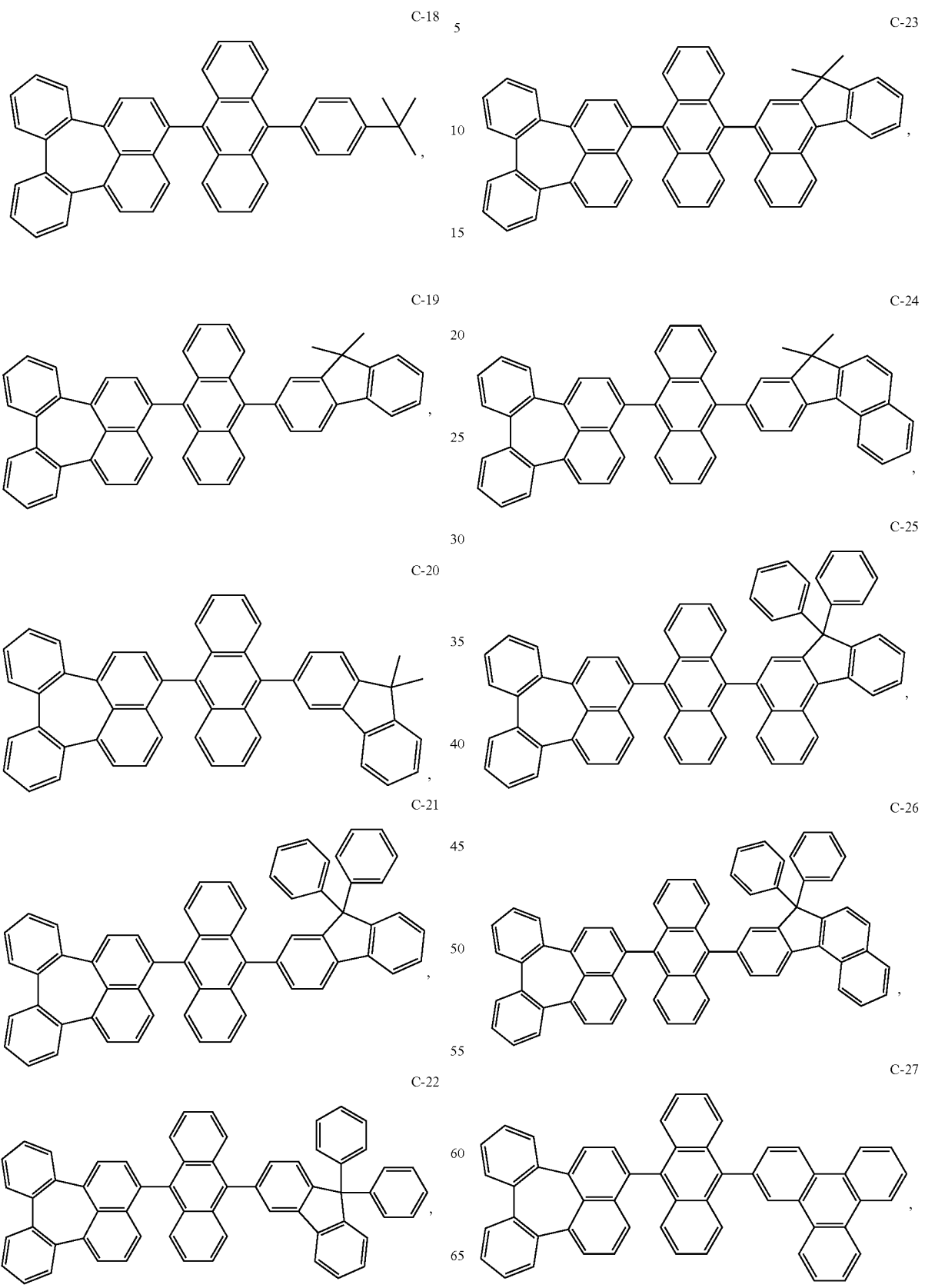

C-28
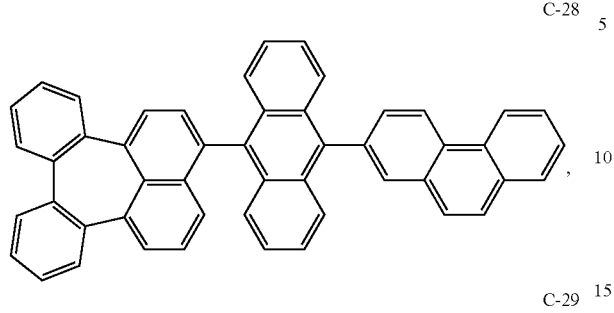
C-29
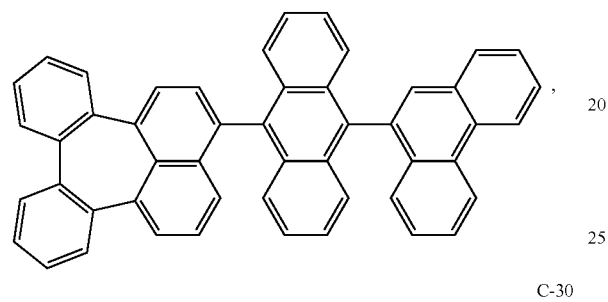
C-30
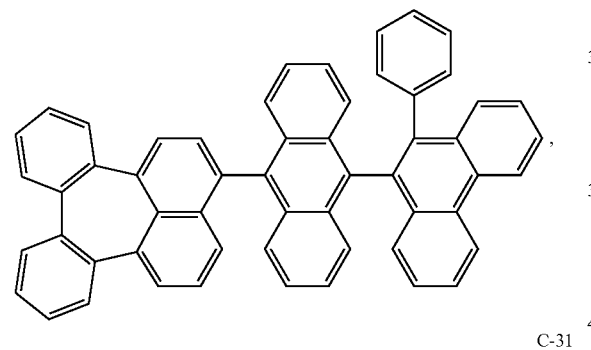
C-31
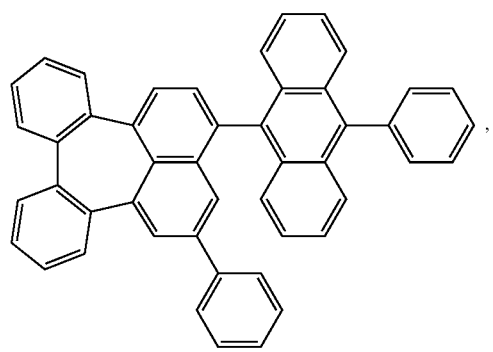
C-32
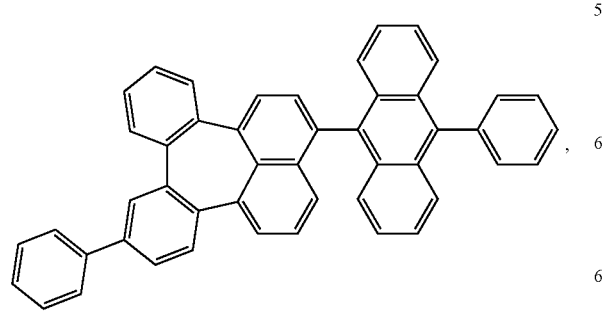
C-33
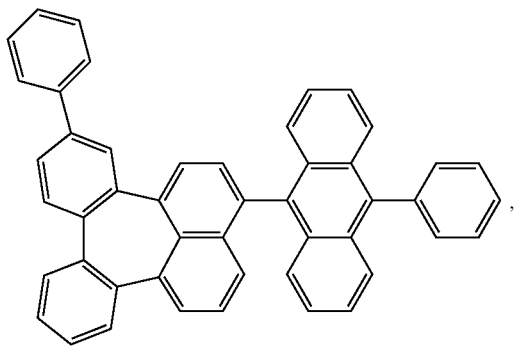
C-34
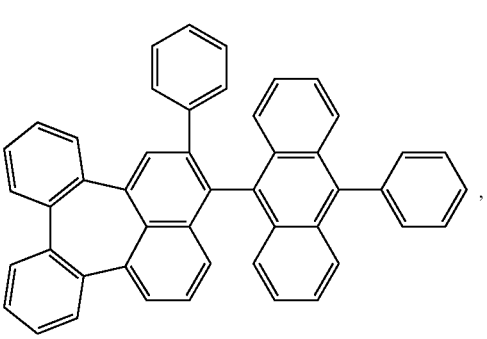
C-53
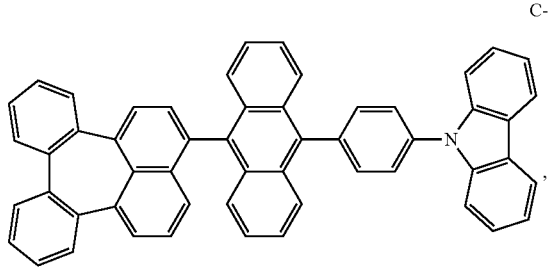
C-54
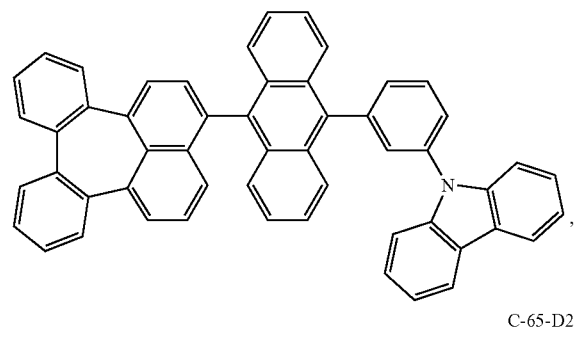
C-65-D26
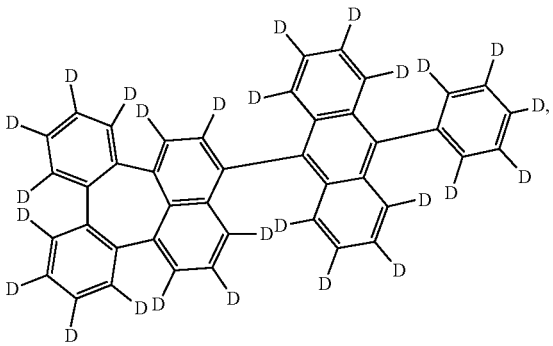

C-65-D13
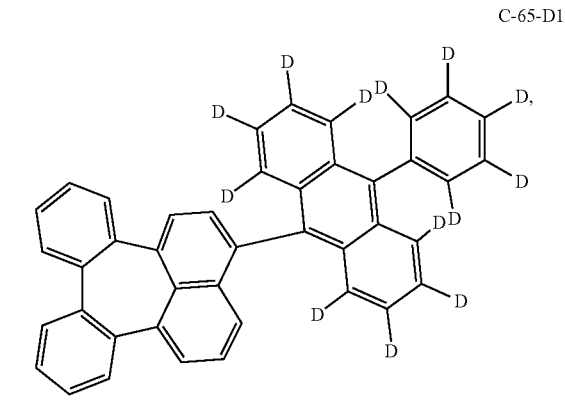
C-72
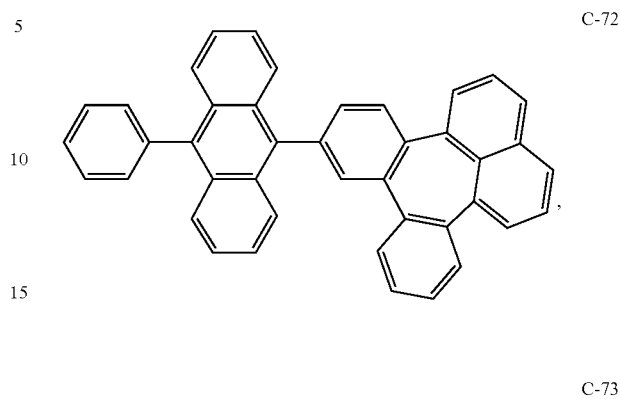
C-66
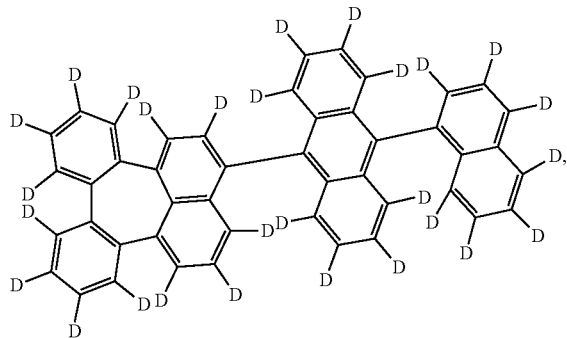
C-73
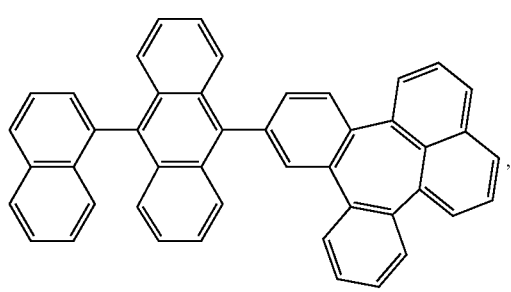
C-67
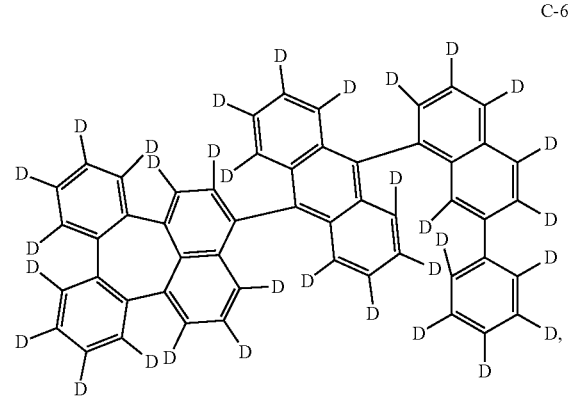
C-74
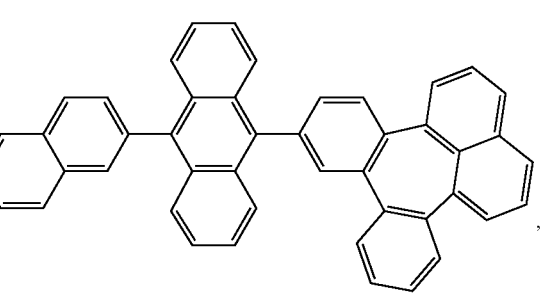
C-75
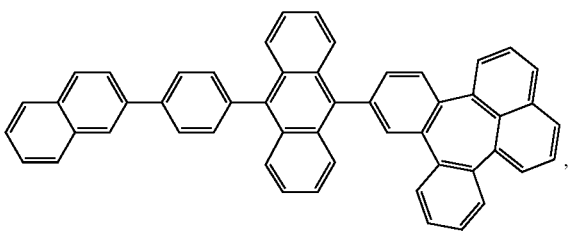
C-71
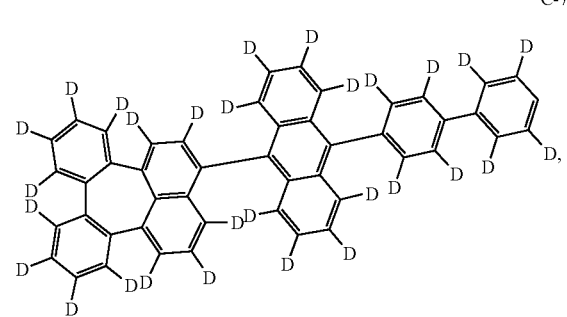
C-76
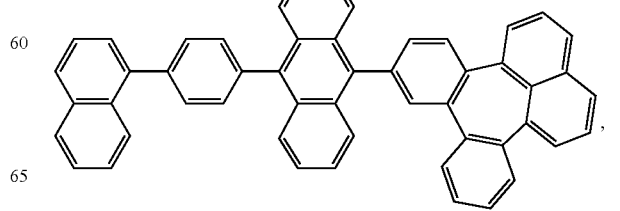

C-77 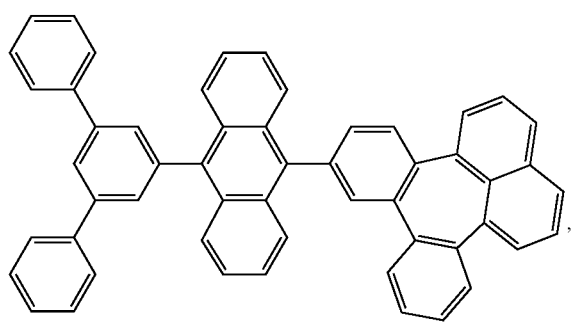
C-78
C-79
C-80
C-81 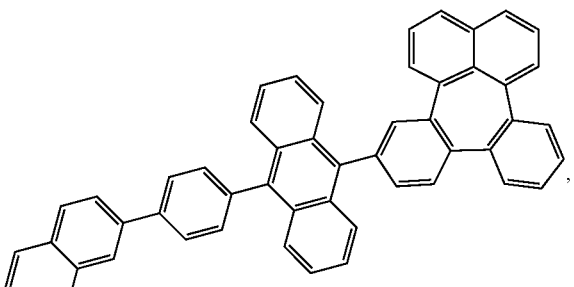
C-82
C-83
C-84
C-85

C-86

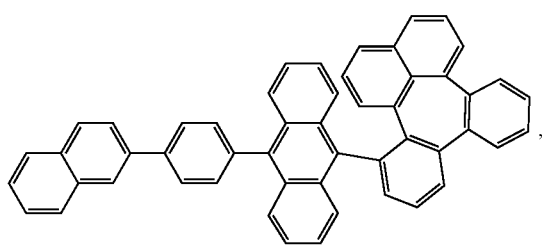

C-87

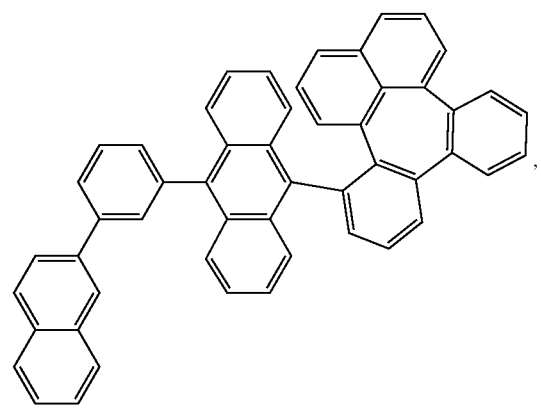

C-88

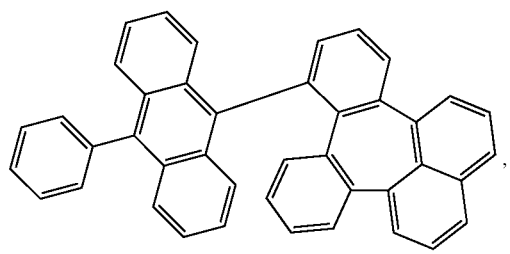

C-89

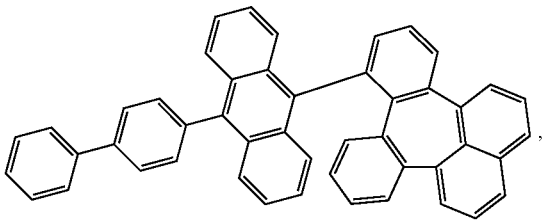

C-90

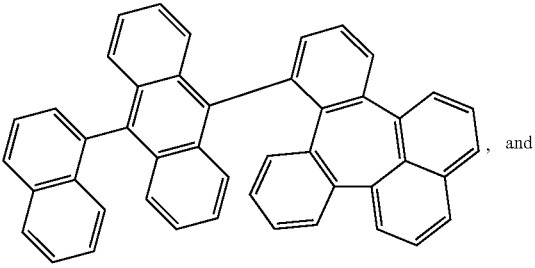

, and

C-91

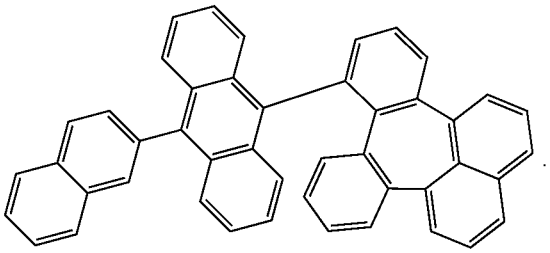

.

4. An organic electroluminescent material comprising the organic electroluminescent compound according to claim 1.

5. An organic electroluminescent device comprising the organic electroluminescent compound according to claim 1.

6. The organic electroluminescent device according to claim 5, wherein the organic electroluminescent compound is comprised in a light-emitting layer.

* * * * *